(12) United States Patent
Matthews

(10) Patent No.: US 11,793,545 B2
(45) Date of Patent: Oct. 24, 2023

(54) ADDUCTOR CANAL BLOCK INTRODUCER

(71) Applicant: Daniel E. Matthews, Fairhope, AL (US)

(72) Inventor: Daniel E. Matthews, Fairhope, AL (US)

(*) Notice: Subject to any disclaimer, the term of this patent is extended or adjusted under 35 U.S.C. 154(b) by 569 days.

(21) Appl. No.: 16/869,110

(22) Filed: May 7, 2020

(65) Prior Publication Data
US 2020/0316345 A1  Oct. 8, 2020

Related U.S. Application Data

(63) Continuation of application No. 16/841,903, filed on Apr. 7, 2020, now abandoned.
(Continued)

(51) Int. Cl.
*A61B 17/34* (2006.01)
*A61M 19/00* (2006.01)
(Continued)

(52) U.S. Cl.
CPC ...... *A61B 17/3421* (2013.01); *A61B 17/3401* (2013.01); *A61B 17/3415* (2013.01); *A61M 19/00* (2013.01); *A61M 25/0074* (2013.01); *A61M 25/0082* (2013.01); *A61M 25/065* (2013.01); *A61M 2025/0089* (2013.01); *A61M 2025/09116* (2013.01); *A61M 2202/048* (2013.01)

(58) Field of Classification Search
CPC ............ A61B 17/3421; A61B 17/3401; A61B 17/3415; A61B 17/29; A61B 2017/00353; A61B 2017/2926; A61B 17/3417; A61M 19/00; A61M 25/0074; A61M 25/0082; A61M 25/065; A61M 2025/0089; A61M 2025/09116; A61M 2202/048
See application file for complete search history.

(56) References Cited

U.S. PATENT DOCUMENTS

| 5,976,110 A | 11/1999 | Greengrass |
| 6,456,874 B1 | 9/2002 | Hafer |

(Continued)

FOREIGN PATENT DOCUMENTS

| EP | 0688182 B1 | 11/2003 | |
| WO | WO-9937224 A1 | * 7/1999 | ............. A61B 17/24 |

OTHER PUBLICATIONS

Continuous Adductor Canal & Periarticular Nerve Block for Total Knee Arthroplasty Matthews' Placement Guide; Avanos Medical, Inc.; Dr. Daniel E. Matthews, M.D.; Apr. 1, 2018.

*Primary Examiner* — Lauren P Farrar
*Assistant Examiner* — Hamza A Darb
(74) *Attorney, Agent, or Firm* — Neustel Law Offices

(57) ABSTRACT

A nerve block introducer for introducing a catheter and also administering an initial dose of local anesthetic, the introducer having an elongated body with a distal end and a proximal end, an inlet, and at least one discharge opening for the local anesthetic near the distal end. The introducer also includes a grasping member near the distal end of the elongated body, the grasping member operably coupled to a handle near the proximal end of the elongated body such that the grasping member can be used to releasably hold a catheter by operation of the handle. The catheter may thus be positioned and left in place following removal of the introducer.

17 Claims, 29 Drawing Sheets

Related U.S. Application Data

(60) Provisional application No. 62/830,841, filed on Apr. 8, 2019.

(51) Int. Cl.
*A61M 25/00* (2006.01)
*A61M 25/06* (2006.01)
*A61M 25/09* (2006.01)

(56) References Cited

U.S. PATENT DOCUMENTS

| | | |
|---|---|---|
| 9,364,607 B2 | 6/2016 | Aguado |
| 9,498,595 B2 | 11/2016 | Spiel |
| 9,814,857 B2 | 11/2017 | Guzman |
| 2006/0167436 A1* | 7/2006 | Geisler ............ A61M 25/0113 606/108 |
| 2008/0058757 A1 | 3/2008 | Pajunk |
| 2009/0099660 A1 | 4/2009 | Scifert |
| 2014/0025039 A1* | 1/2014 | Rajendran ............ A61M 19/00 604/512 |
| 2015/0367103 A1 | 12/2015 | Pajunk |
| 2016/0157701 A1* | 6/2016 | Preis ................ A61B 17/29 600/106 |
| 2017/0049993 A1 | 2/2017 | Cosman |
| 2020/0268413 A1* | 8/2020 | Khalaj ............... A61M 25/02 |

* cited by examiner

ADDUCTOR CANAL BLOCK INTRODUCER

CROSS REFERENCE TO RELATED APPLICATIONS

The present application is a continuation of U.S. application Ser. No. 16/841,903 filed on Apr. 7, 2020, which claims priority to U.S. Provisional Application No. 62/830,841 filed Apr. 8, 2019. Each of the aforementioned patent applications, and any applications related thereto, is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to an adductor canal block introducer for introducing a catheter in a position to provide local anesthetic to a target nerve or nerves.

Related Art

Post-surgical pain is ordinarily treated by opioid analgesics and regional pain blocks (i.e. single shot blocks; long-lasting locals, and bolus or continuous drip anesthetics). Regional pain blocks are typically performed by the anesthesiologist under ultrasound guidance in the hours before (block room), in the operating suite, or after (post-op room) surgery. The bolus or continuous drip regional pain block procedure consists of passing the tip of a small diameter catheter through the skin (percutaneously) and into the vicinity of the target nerve. The proximal end of the catheter is then fastened to a pump that is maintained external to the patient's body. The pump contains a local anesthetic (i.e. lidocaine, ropivacaine, bupivacaine, etc.) and functions to bathe the target nerve (or nerves) in the anesthetic for a period of days post-surgery, and in a home care environment.

Any discussion of the related art throughout the specification should in no way be considered as an admission that such related art is widely known or forms part of common general knowledge in the field.

SUMMARY

Bolus and continuous drip regional nerve blocks are frequently used to mitigate painful sensations following joint surgery, including following total knee arthroplasty (TKA). In this case, the catheter tip for introducing nerve blocks is placed by an anesthesiologist nearby a nerve in 1 of 3 locations: 1. Femoral nerve in the upper thigh; 2. Distal femoral nerve just proximal to the adductor canal; or 3. The Saphenous nerve within the adductor canal. Various insertion techniques (i.e. perpendicular vs. oblique approach to nerve) have been used historically to reduce catheter migration and to prolong pain management.

Orthopedic surgeons have recently started to place catheters for regional nerve blocks in the operating room, and without ultrasound guidance. Despite the surgeon's enthusiasm and skills, it is evident that surgeons may not have the tools on-hand to reliably and safely place catheters intraoperatively. For example, some tools for catheter placement, such as pituitary rongeurs, have different head and shaft lengths, different head and shaft widths, different head angles, and different mouth sharpness, etc. Similarly, the lack of a set of standardized tools can place a significant burden on the surgical staff and administration to compile and maintain the correct set of instruments to assure safe and reliable catheter placement. Surgeons are often supplied with insufficient/incorrect instruments, causing misplaced and/or damaged catheters.

Disclosed herein is an adductor canal block introducer (i.e., the Matthews Adductor Canal Block Introducer) that allows the surgeon to reproducibly perform these blocks in a reproducible, efficient, efficacious manner without the need for ultrasonic or electrical guidance. This can be very important for post-operative pain management and patient care in environments where anesthesia services are not available to perform these services. Using the disclosed device, the surgeon may also eliminate the additional anesthesia procedure as the catheter is placed during the surgical procedure.

An example embodiment is directed to a nerve block introducer system, which can be used to introduce catheters and anesthetic agents in the adductor canal or elsewhere in the body of a patient. The nerve block introducer system may comprise a cannula having an elongated body with a distal end, a proximal end, and a slot extending along the elongated body, the slot having two sides and a lower surface; a cannulated trocar positioned in the slot of the cannula between the two sides, the cannulated trocar having a distal end and a proximal end, wherein the distal end of the cannulated trocar is near the distal end of the cannula, the proximal end comprising an inlet and the distal end comprising at least one discharge proximate to the distal end, wherein the inlet and the at least one discharge are in fluid communication with each other; and a catheter positioned in the slot of the cannula and held in place by the cannulated trocar, the two sides of the slot, and the lower surface of the slot, the catheter comprising a proximal end and a distal end near the distal end of the cannula.

The distal end of the cannulated trocar may extend beyond the distal end of the cannula, and the at least one discharge may comprise a plurality of openings, and the plurality of openings may be located beyond the distal end of the cannula. Further, the plurality of openings may be located laterally on an outer surface of the cannulated trocar.

In some embodiments, the inlet is adapted for attachment of a syringe such that the syringe can be used to introduce an anesthetic agent into the inlet.

In some example embodiments, the cannulated trocar may be removably positioned in the slot, such that the cannulated trocar can be removed by sliding lengthwise along the slot (for example, by withdrawing it backward, away from the distal end of the cannula). Further, in some embodiments the cannulated trocar is sized and positioned such that the catheter is held in place in the slot by an interference fit.

In some example embodiments of the nerve block introducer system, the slot may comprise a first slot portion and a second slot portion, such that the first slot portion has a larger opening between the two sides than the second slot portion, the second slot portion being positioned below the first slot portion. In such embodiments, the cannulated trocar may have a larger diameter than the catheter, and the cannulated trocar may fit in the first slot portion and hold the catheter securely in the second slot portion, for example, by an interference fit.

Any system or components described herein may, for example, be used by inserting the distal end of the cannula into a body cavity such that the distal end of the cannula and the distal end of the catheter are positioned near a selected location in the body cavity. The method may also include attaching a fluid source to the inlet of the cannulated trocar such that the fluid source (which may be a syringe, pump, etc.) is in fluid communication with the inlet, using the fluid source to infuse an anesthetic agent into the body cavity via the at least one discharge, removing the cannulated trocar from the cannula by sliding it out of the slot and away from the body cavity, and removing the cannula from the body cavity, such that the catheter is left in the body cavity with its distal end near a nerve or multiple nerves.

In some applications of the method, the body cavity may be an adductor canal, wherein the distal end of the catheter extends beyond the distal end of the cannula. The method may further comprise rotating the cannula rotating the cannula so that the catheter can be held in place against the femur when the cannula is removed after the cannulated trocar has been removed, so that the distal end of the catheter remains in a desired location when the cannula is removed.

In another embodiment, the nerve block introducer system may comprise a grasper rather than a slotted cannula. The grasper may include a proximal end and a distal end. The grasper may have a pair of handles with finger loops that operate a grasping mechanism at or near a distal end of the grasper. The grasping mechanism may further comprise two grasping members, which can be used to hold a catheter in the instrument until a user places the catheter in a desired location. The grasper may include an elongated member that extends from the proximal end to near the distal end, although it may not necessarily reach the distal end.

The elongated member may be hollow, with a cavity or channel to fluidly connect an inlet near the proximal end of member, and a discharge near the distal end of the member. The inlet may also be sized or adapted for attachment of a fluid source, such as a pump or a syringe, and may also include a standard locking mechanism to hold the syringe.

Since the inlet is in fluid communication with the discharge (which may comprise a plurality of openings) via the channel, a syringe, or any other fluid source, may be used to force fluid, such as an anesthetic agent, through the elongated member and out through the discharge, near the distal end of the grasper.

As discussed above, the discharge of the grasper may comprise a plurality of openings, which may be placed or located laterally around the outer surface of the elongated member, which surface may be a partial cylinder. The elongated member may be or comprise a fixed portion of the grasping member, with one grasping member near the distal end. The two grasping members may have slightly concave interior surfaces, such that they can be used to hold a catheter near the distal end without damaging it. The grasper may also have a movable grasping member that is operable by the handles.

There has thus been outlined, rather broadly, some of the embodiments of the adductor canal block introducer in order that the detailed description thereof may be better understood, and in order that the present contribution to the art may be better appreciated. There are additional embodiments of the adductor canal block introducer that will be described hereinafter and that will form the subject matter of the claims appended hereto. In this respect, before explaining at least one embodiment of the adductor canal block introducer in detail, it is to be understood that the adductor canal block introducer is not limited in its application to the details of construction or to the arrangements of the components set forth in the following description or illustrated in the drawings. The adductor canal block introducer is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
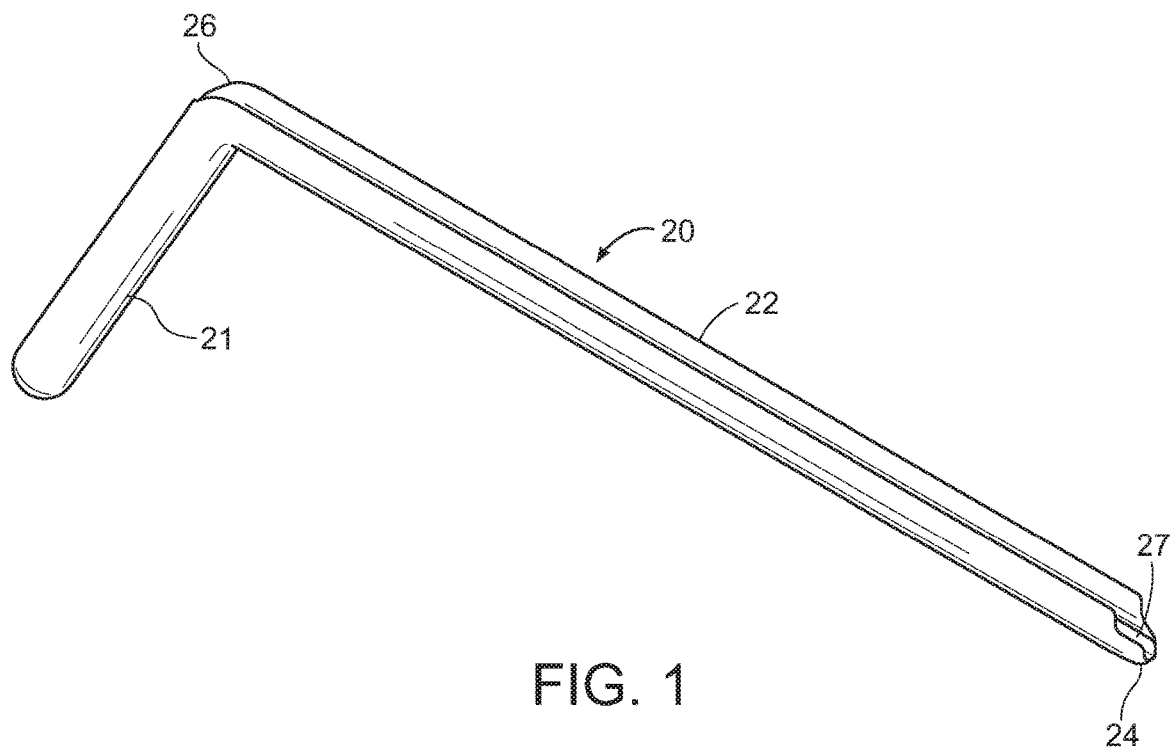
FIG. 1 is a perspective view of an introducer in accordance with an example embodiment.

A. Overview.

An example adductor canal block introducer system (or more generally, nerve block introducer system) generally comprises a cannula 20 having an elongated body 22 with a distal end 24, a proximal end 26, and a slot 27 extending along the elongated body 22, the slot having two sides 28 and a lower surface 29. The components referenced herein may be either reusable or disposable. The system 10 may also include a cannulated trocar 30 positioned in the slot 27 of the cannula 20 between the two sides, the cannulated trocar 30 having a distal end 32 and a proximal end 34, wherein the distal end 32 of the cannulated trocar 30 is near the distal end 24 of the cannula 20, the proximal end 34 comprising an inlet 36 and the distal end 32 comprising at least one discharge 38 proximate to the distal end 32, wherein the inlet 36 and the at least one discharge are in fluid communication with each other, such as via a channel or cavity 39. The system may also include a catheter 40 positioned in the slot 27 of the cannula 20 and held in place by the cannulated trocar 30, the two sides 28 of the slot 27, and the lower surface 29 of the slot 27, the catheter 40 comprising a proximal end 42 and a distal end 42 near the distal end 24 of the cannula 20.

The distal end 32 of the cannulated trocar 30 may extend beyond the distal end 24 of the cannula, and the at least one discharge 38 may comprise a plurality of openings 33, and the plurality of openings 33 may be located beyond the distal end 24 of the cannula 20. Further, the plurality of openings 33 may be located laterally on an outer surface 37 of the cannulated trocar 30.

In some embodiments, the inlet 36 is adapted for attachment of a fluid source, such as a syringe 50, such that the syringe 50 can be used to introduce an anesthetic agent 52 into the inlet 36. In some example embodiments, the cannulated trocar 30 may be removably positioned in the slot 27, such that the cannulated trocar 30 can be removed by sliding lengthwise along the slot 27 (for example, by withdrawing it backward, away from the distal end of the cannula). Further, in some embodiments the cannulated trocar 30 is sized and positioned such that the catheter 40 is held in place in the slot 27 by an interference fit.

In some example embodiments of the introducer system 10, the slot 27 may comprise a first slot portion 27a and a second slot portion 27b, such that the first slot portion 27a has a larger opening between the two sides 28a than the two sides 28b of the second slot portion 27b, the second slot portion 27b being positioned below the first slot portion 27a. In such embodiments, the cannulated trocar 30 may have a larger diameter than the catheter 40, and the cannulated trocar 30 may fit in the first slot portion 27a and hold the catheter 40 securely in the second slot portion 27b, for example, by an interference fit. The interference fit holds the catheter 40 firmly in place because the distance between the surface of the cannulated trocar 30 and the lower surface 29 of the slot 27 is slightly smaller than the diameter or width of the catheter 40.

B. Cannula.

Figure 2:
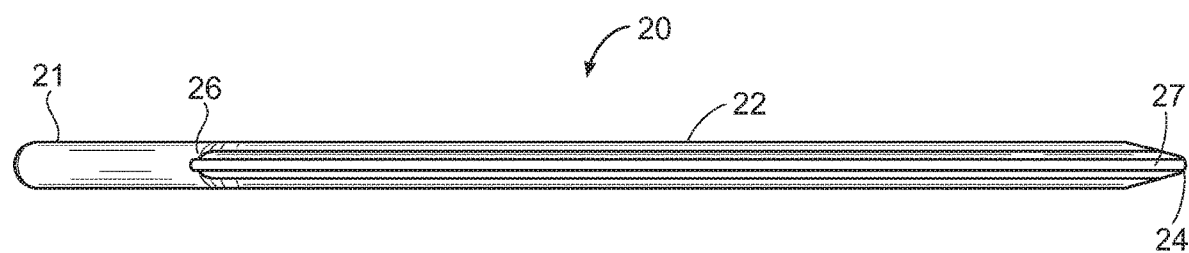
FIG. 2 is a top view of an introducer in accordance with an example embodiment.
Figure 3:
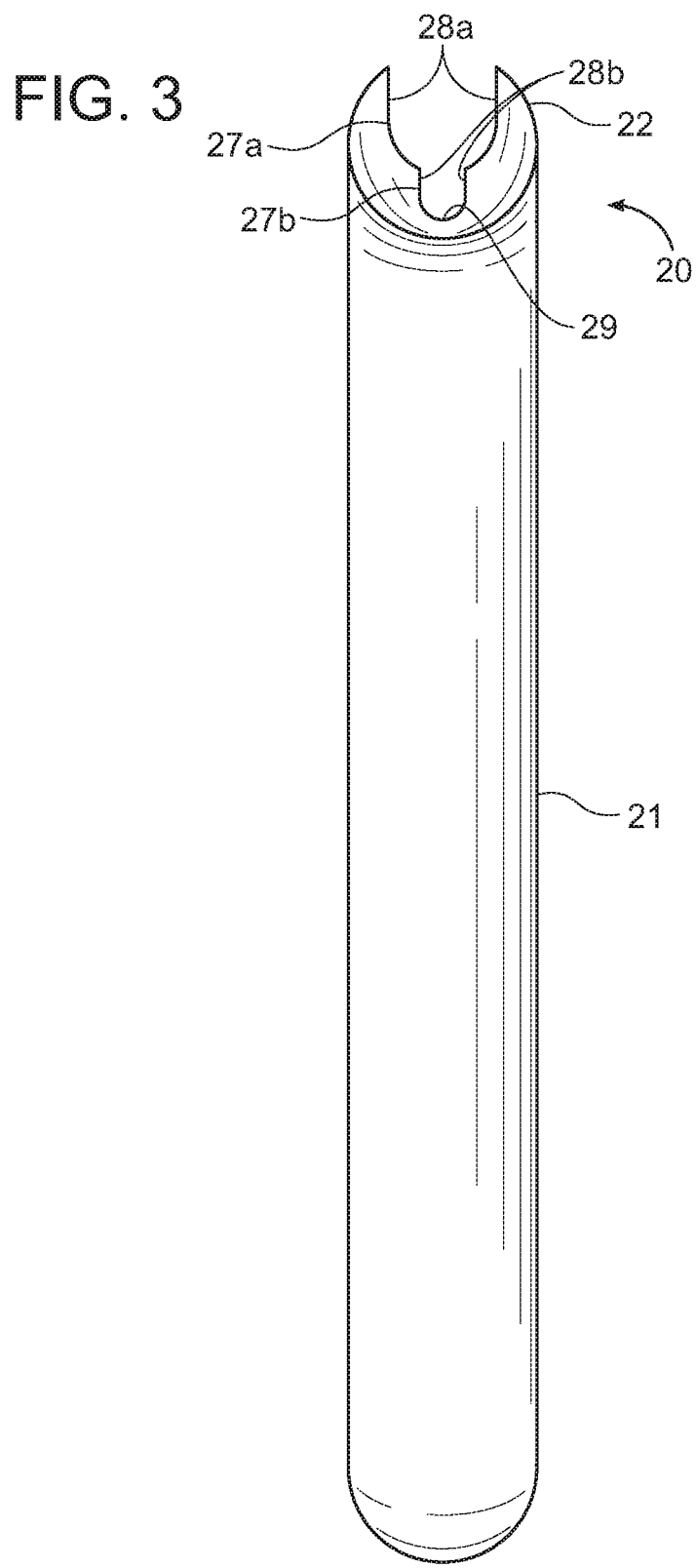
FIG. 3 is a side view of an introducer in accordance with an example embodiment.

As shown in FIGS. 1-16, one example embodiment of the introducer system 10 includes a slotted cannula 20, best shown in FIGS. 1-3. The cannula and the trocar may be either reusable or disposable. The cannula generally has an elongated body 22 with a distal end 24, a proximal end 26, and a slot 27 extending along the elongated body 22, the slot having two sides 28a, 28b, and a lower surface 29. In addition, the cannula 20 may be rigid to facilitate introduction of a catheter 40 into a body cavity, such as an adductor canal. The two sides 28 of the slot 27 may be vertical, and the lower surface 29 may be rounded. The upper portion of the side edges of the cannula may be rounded as well, as also shown, and the side edges may form an angled and rounded tip at or near the distal end 24 of the cannula 20. The slot 27 may be open all the way to the proximal end of the cannula 20, as shown, such that the trocar 30 may be removed without obstruction by sliding it in the slot 27 rearward, such that the distal end 32 of the cannulated trocar 30 is withdrawn along the slot, from the distal end 24 toward the proximal end 26 of the cannula 20.

In addition, the two sides 28a, 28b may each be in multiple planes, to create multiple slot portions (i.e., portions having different widths), as will be described below. The cannula may also include a handle 21, extending at an angle away from the elongated body 22, so that a surgeon can readily grasp the cannula 20 by the handle 21 when preparing it for use, or using it to introduce a catheter 40 into a body cavity, such as the adductor canal. For example, the handle 21 may be integrally formed with the body 22 of the cannula 20, and form an angle of about 120° with the body 22, although other angles are possible. The handle 21 may be of any suitable length, such as about 6 centimeters.

Figure 8:
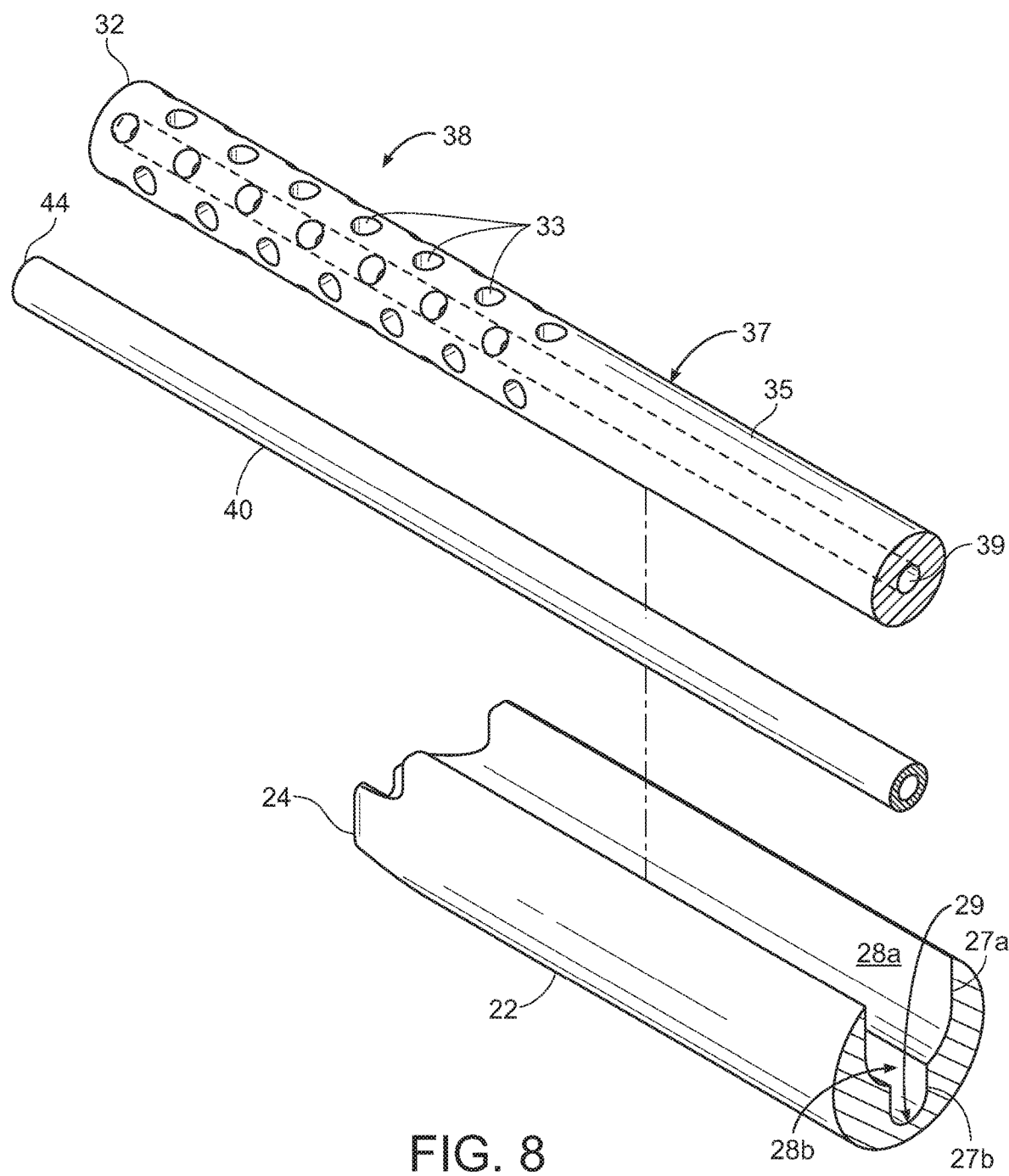
FIG. 8 is an exploded perspective view of one end of an introducer system in accordance with an example embodiment.

The elongated body 22 may be of any suitable length, depending on the application. For example, the body 22 may be about 16 centimeters, which length may be used as a guide for where to position a catheter 40, as will be discussed further below. As also shown, the cannula 20 may include a slot 27 that extends along the body 22, from the proximal end 26 to the distal end 24. As mentioned, the slot 27 may have two sides 28 and a lower surface 29, with the slot 27 being open at the top side of the cannula 20. The slot 27 may have a single width, or it may have a larger, upper or first slot portion 27a and a smaller second slot portion 27b, as best shown in FIGS. 3 and 8.

Figure 7:
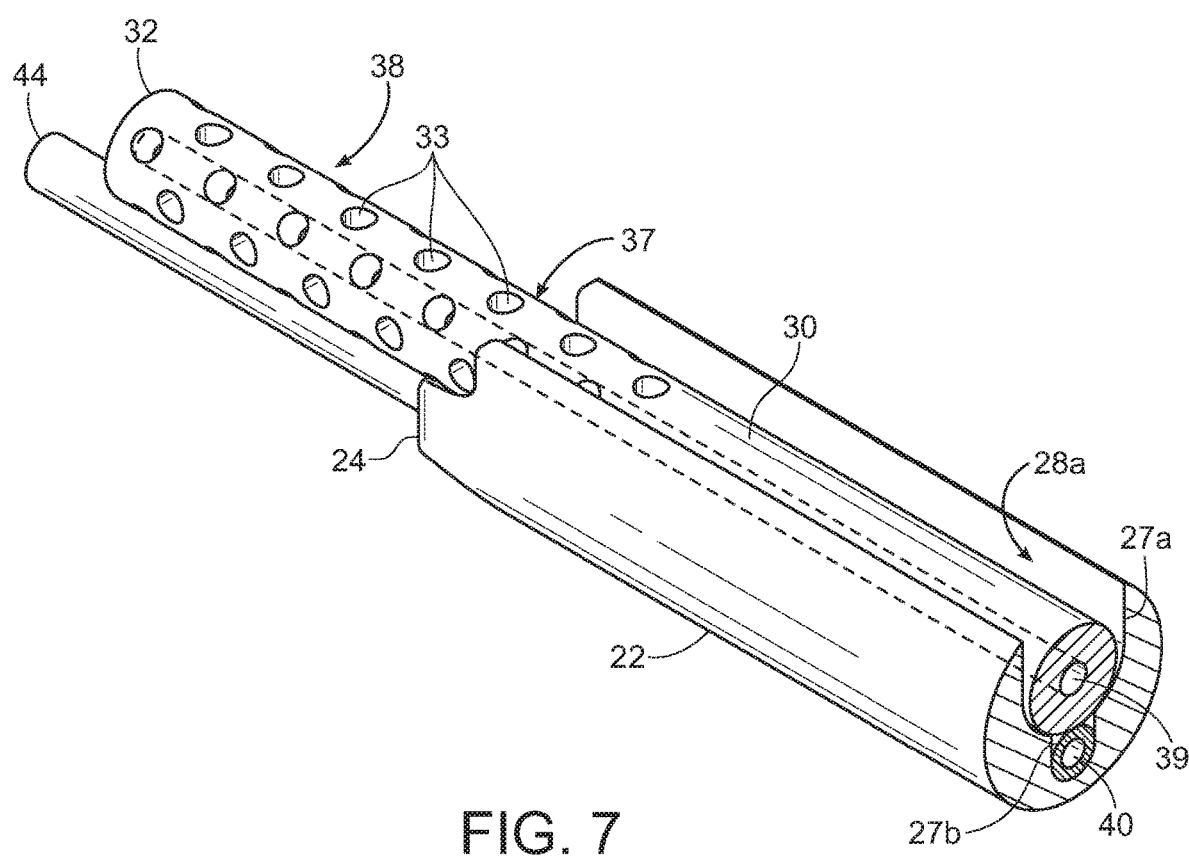
FIG. 7 is a detailed perspective view of one end of an introducer system in accordance with an example embodiment.

The two slot portions 27a and 27b may be sized specifically to be used with the other components of the introducer system 10. Each slot portion 27a, 27b may comprise two sides 28a and 28b, respectively. For example, the first slot portion 27a may be sized to accommodate and securely hold cannulated trocar 30. Although various sizes are possible, the diameter of trocar 30 may be about 3 mm, in which case the slot 27 or the first slot portion 27a may be about 2⅔ mm, such that the cannulated trocar 30 fits securely within the first slot portion 27a. Similarly, the lower or second slot portion 27b may be smaller, so that it holds catheter 40 (e.g., a 7FR catheter) in position, especially when trocar 30 is in place, as shown in FIGS. 7-8. However, the second portion 27b of the slot 27 need not be smaller than the diameter of catheter 40, and if it is not, that may make for easier detachment from the cannula 20 and placement of the catheter 40, as will be described further below. With the slot proportions noted above, the slot 27 may have an overall depth of about 5 mm, although as noted, other dimensions are possible.

C. Cannulated Trocar.

Figure 4:
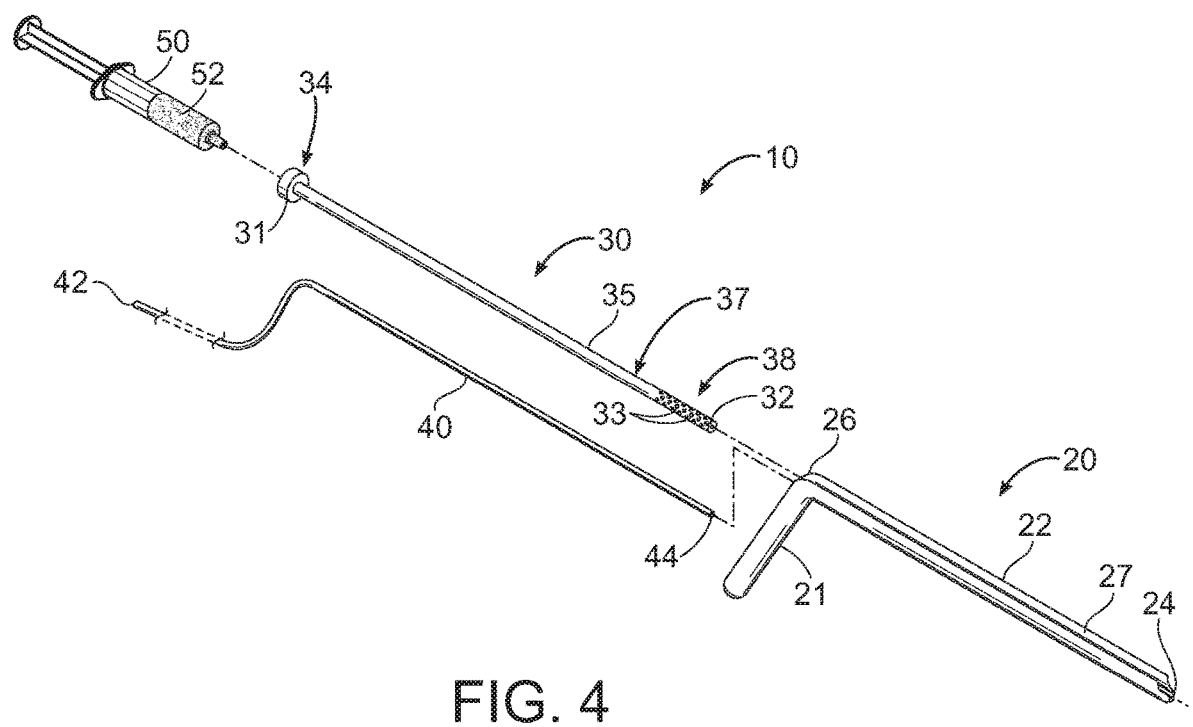
FIG. 4 is an exploded view of an introducer in accordance with an example embodiment.
Figure 5:
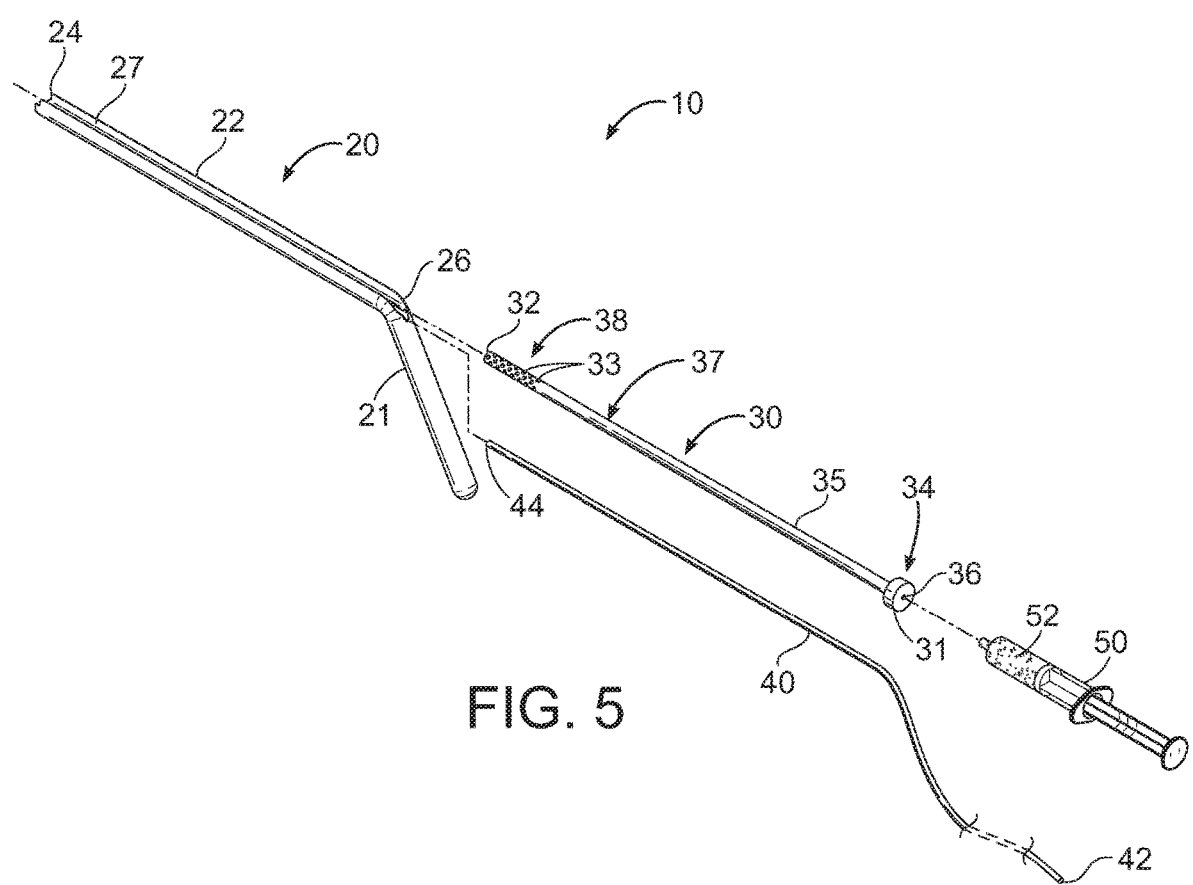
FIG. 5 is another exploded view of an introducer in accordance with an example embodiment.
Figure 6:
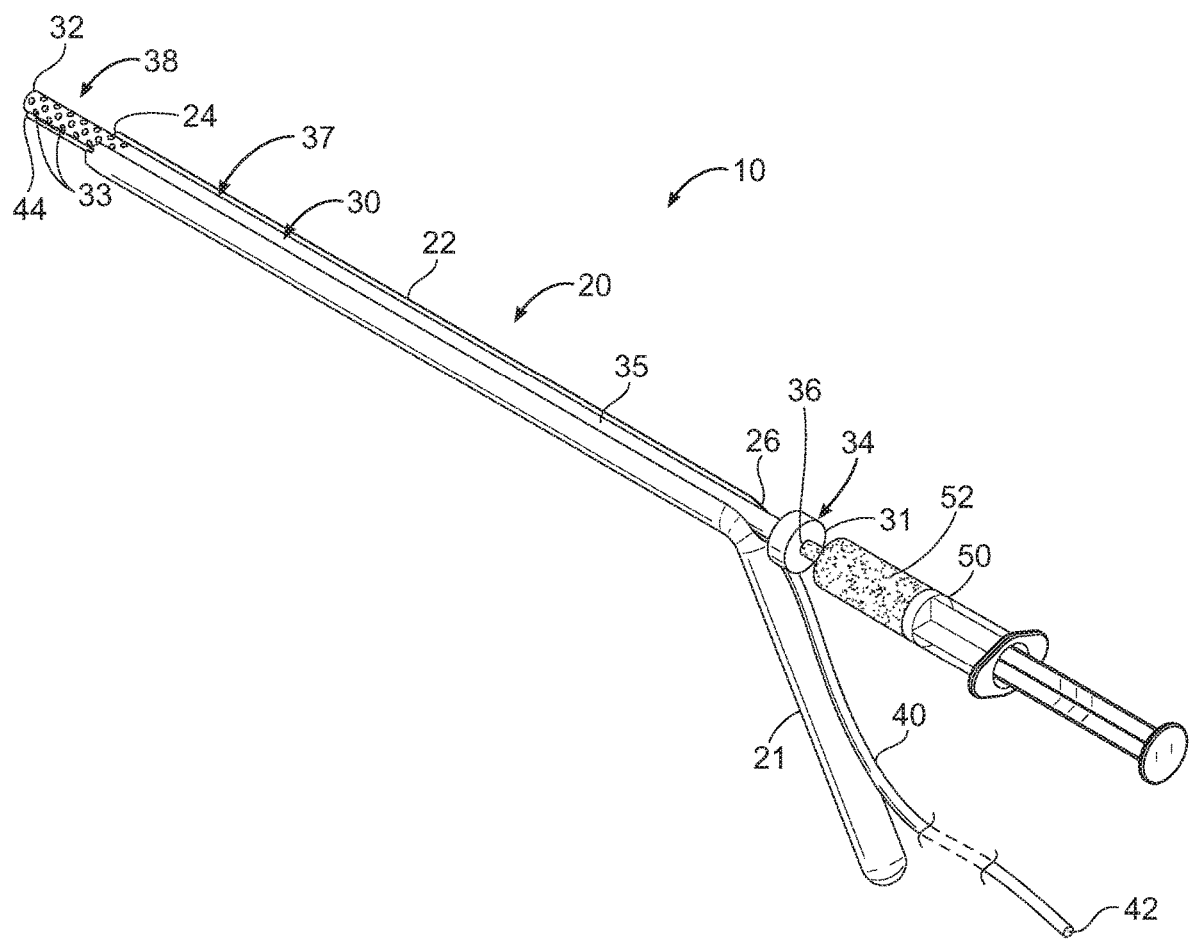
FIG. 6 is a perspective view of an assembled introducer system in accordance with an example embodiment.

The introducer system 10 also includes a cannulated trocar 30. The cannulated trocar 30, like the slotted cannula 20, also has a proximal end 34 and a distal end 32, which ends correspond to the same ends of the slotted cannula 20 when the system is assembled as shown in FIGS. 4-6. The cannulated trocar 30 includes an inlet 36 at or near the proximal end 34, and a discharge 38 at or near the distal end 32. The cannulated trocar 30 may be in the general form of an elongated hollow tube, with a cavity or channel 39 connecting the inlet 36 to the discharge 38, such that the inlet 36 is in fluid communication with the discharge 38. The cannulated trocar 30 may comprise a body 35, which may be in the general form of a rigid tube having a single diameter over most of the length of the cannulated trocar 30, as shown in FIGS. 4-6. In the example noted above, the diameter may be about 3 mm, and the diameter may be generally constant along the length of the cannulated trocar 30, so that the trocar 30 may be smoothly and easily withdrawn by pulling it rearward out of the slotted cannula 20, along and out of the slot 27.

The inlet 36 of the trocar 30 may be sized or adapted for attachment of a fluid source, such as a pump or a syringe 50, and may also include a standard locking mechanism to hold the syringe 50. A syringe, such as a 10 cc syringe, may be provided in a kit having the components necessary for the procedures described herein, and may be filled with 0.5% ropivacaine, for example. Since the inlet 36 is in fluid communication with the discharge 38 (which may comprise a plurality of openings 33) via channel 39, the syringe 50, or any other fluid source, may be used to force fluid, such as an anesthetic agent, through the cannulated trocar 30 and out through the discharge 38, near the distal end 32 of the trocar and the distal end 24 of the slotted cannula 20. Due to the relatively large diameter of the trocar 30 (as compared to a catheter), it may be much easier for a surgeon to introduce a single bolus of nerve blocking agent 52 at the desired location (e.g., adductor canal), rather than only relying on the catheter to do so initially, even though the catheter may later provide for continuous introduction of medication (e.g., continuous drip) or electricity to the nerves around the knee joint including the posterior nerves of the knee joint capsule.

To facilitate introduction of fluid through the cannulated trocar 30, when the system 10 is assembled (i.e., when the cannulated trocar 30 is in position for use), the distal end 32 of the cannulated trocar 30 may extend beyond the distal end 24 of the slotted cannula 20, as best shown in FIGS. 6-8. Further, the plurality of openings 33 may be located such that they extend beyond the distal end 24 of the slotted cannula 20 when the cannulated trocar 30 is in place for initial introduction of the catheter 40. More specifically, the plurality of openings 33 may be placed or located laterally around the generally cylindrical outer surface 37 of the cannulated trocar 30, and the distribution may extend from the distal end 32, and back about 2 cm along the outer surface 37.

The cannulated trocar 30 may also have a flange 31 at or near its proximal end 34, which may be used by a surgeon to pull and remove it from the slotted cannula 20 by sliding it out of the slot 27 as described herein. The cannulated trocar 30 may have a larger diameter than the catheter 40, and the cannulated trocar 30 may fit in the first slot portion 27a of the cannula 20. Thus configured, the trocar 30 can hold the catheter 40 securely in the second slot portion 27b of the cannula 20, for example, by an interference fit. The interference fit holds the catheter 40 firmly in place when the trocar is in position as shown in FIG. 7 because the distance between the surface of the cannulated trocar 30 and the lower surface 29 of the slot 27 is slightly smaller than the diameter or width of the catheter 40. Thus, the trocar 30, the catheter 40, or both may deform slightly, which will result in the catheter 40 being held securely in position.

D. Grasper Embodiment.

Figure 18:
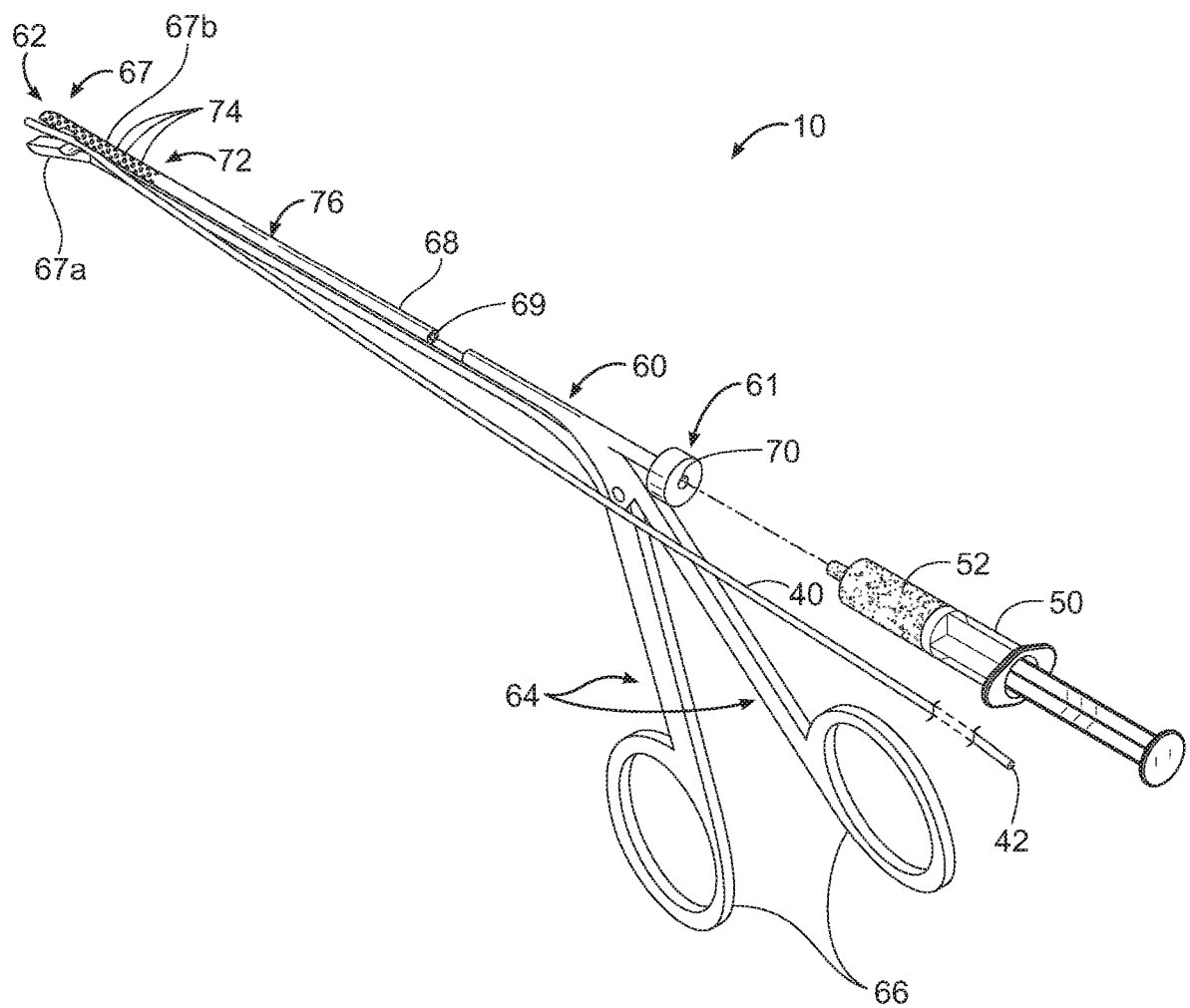
FIG. 18 is a perspective view of an introducer system in use in accordance with another example embodiment.
Figure 19:
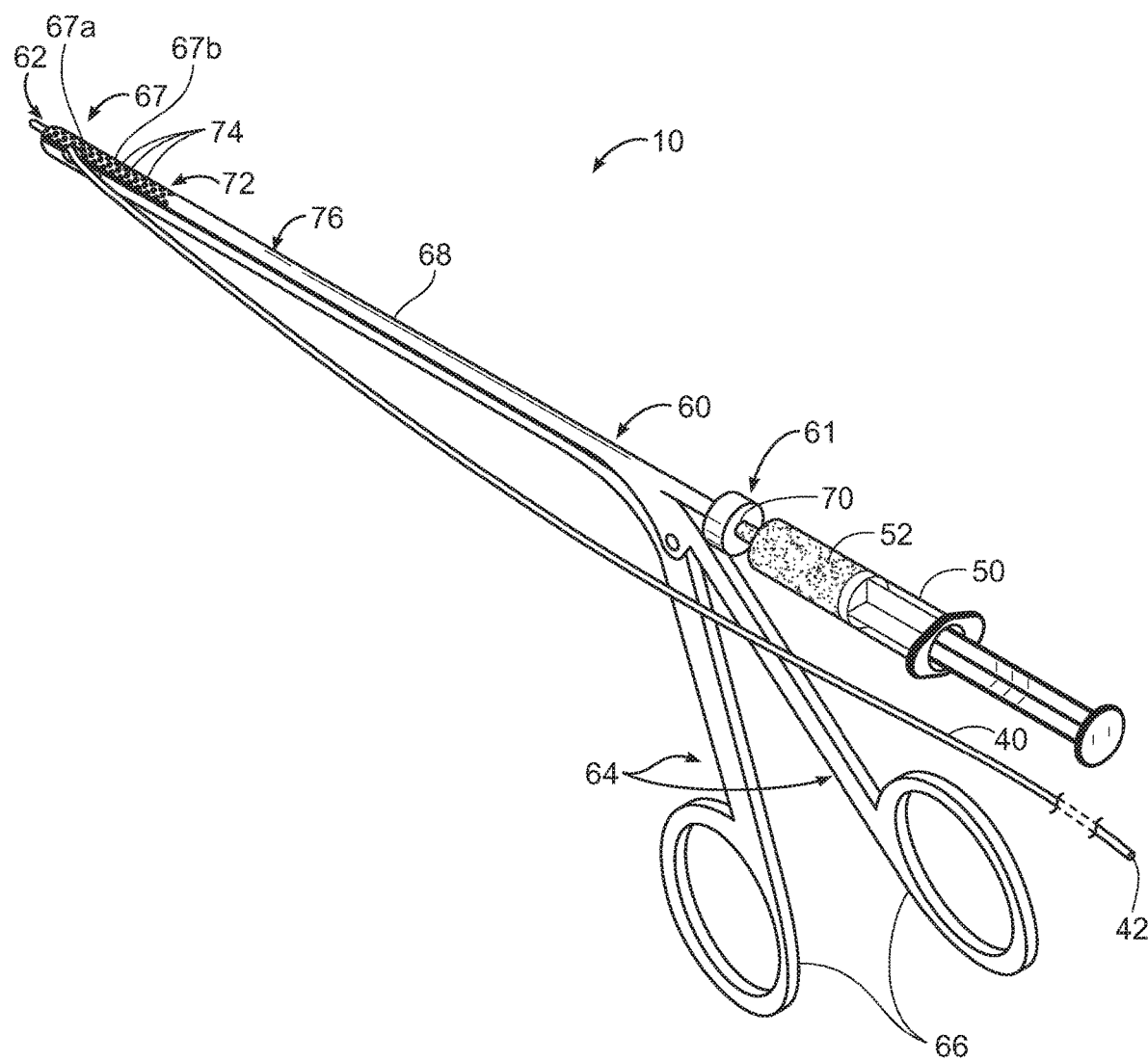
FIG. 19 is another perspective view of an introducer system in use in accordance with another example embodiment.
Figure 20:
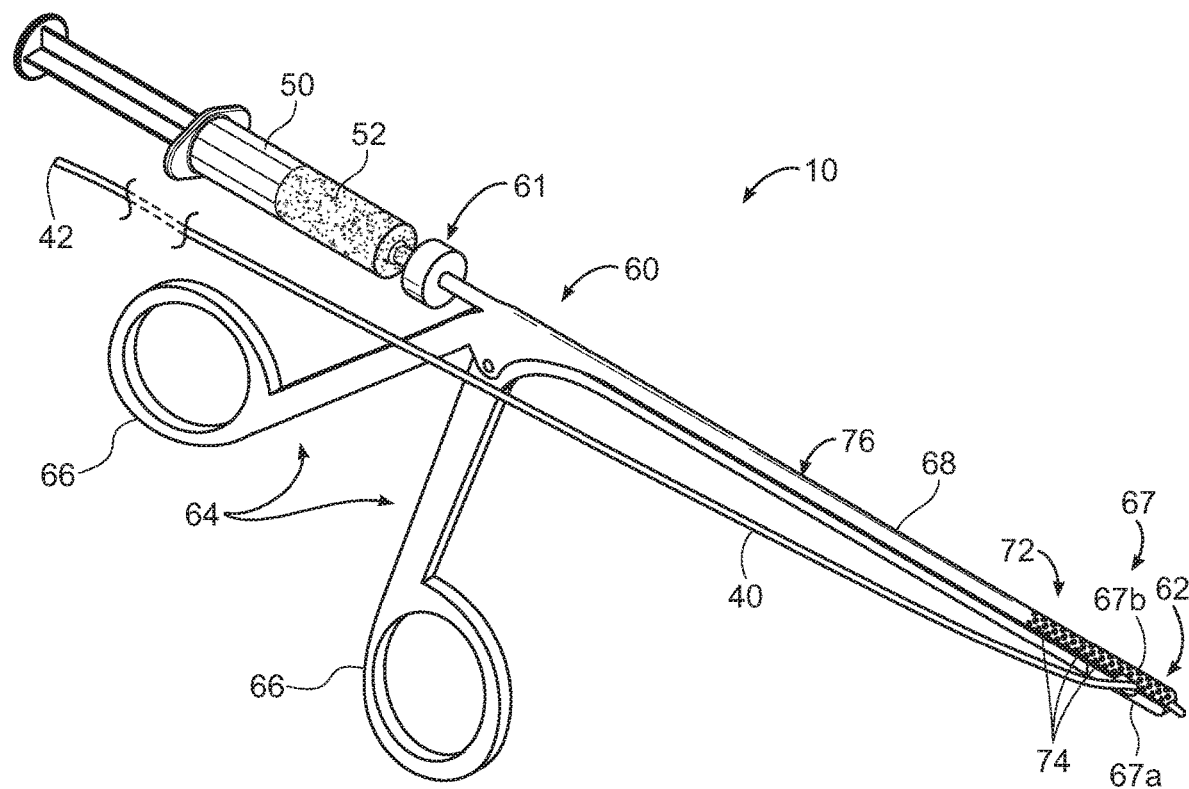
FIG. 20 is another perspective view of an introducer system in use in accordance with another example embodiment.

In another embodiment, the nerve block introducer system 10 may comprise a grasper 60 rather than a slotted cannula. As with the cannula, the grasper may be either reusable or disposable. The grasper 60 may include a proximal end 61 and a distal end 62. As shown in FIGS. 18-20, the grasper may have a pair of handles 64 with finger loops 66 that operate (e.g., close) a grasping mechanism 67 at or near a distal end 62 of the grasper 60. The grasping mechanism 67 may further comprise two grasping members 67a, 67b, which can be used to hold a catheter 40 in the instrument until a user places the catheter 40 in a desired location, such as by direct visualization. The grasper 60 may include an elongated member 68 that extends from the proximal end 61 to near the distal end 62, although it may not necessarily reach the distal end.

The elongated member 68 may be hollow, as shown in the partial sectional view of FIG. 18, with a cavity or channel 69 to fluidly connect an inlet 70 near the proximal end of member 68, and a discharge 72 near the distal end of the member 68. The inlet 70 may also be sized or adapted for attachment of a fluid source, such as a pump or a syringe 50, and may also include a standard locking mechanism to hold the syringe 50.

Since the inlet 70 is in fluid communication with the discharge 72 (which may comprise a plurality of openings 74) via channel 69, a syringe 50, or any other fluid source, may be used to force fluid, such as an anesthetic agent, through the elongated member 68 and out through the discharge 72, near the distal end 62 of the grasper 60. Due to the relatively large diameter or capacity of the channel 69 (as compared to a catheter), it may be much easier for a surgeon to introduce a single bolus of nerve blocking agent 52 at the desired location (e.g., adductor canal), rather than only relying on the catheter to do so initially, even though the catheter 40 may later provide for continuous introduction of medication (e.g., continuous drip) or electricity to the nerves around the knee joint including the posterior nerves of the knee joint capsule.

As discussed above, the discharge may comprise a plurality of openings 74, which may be placed or located laterally around the outer surface 76 of the elongated member, which surface 76 may be a partial cylinder. As shown in FIGS. 18-20, the elongated member 68 may be or comprise a fixed portion of the grasping member, with one grasping member 67a near the distal end 62. As also shown, the grasping members 67a, 67b may have slightly concave interior surfaces, such that they can be used to hold a catheter near the distal end 62 without damaging it. The grasper 60 may also have a movable grasping member 67a that is operable by the handles 64.

The grasping mechanism 67 may operate in a manner similar to pituitary rongeurs, such that the grasping mechanism 67 generally closes when the handles 64 are moved together (as when holding a catheter), and opens when the handles 64 are moved apart. Further, the overall mechanism may have sufficient friction so that the grasper remains closed without being held closed by a user, which may facilitate catheter introduction and placement. As mentioned above, the handles 64 may include finger loops 66 to make the grasper 60 easier to position and operate when introducing a catheter in an adductor canal or other desirable location to introduce nerve block.

E. KIT.

Figure 23:
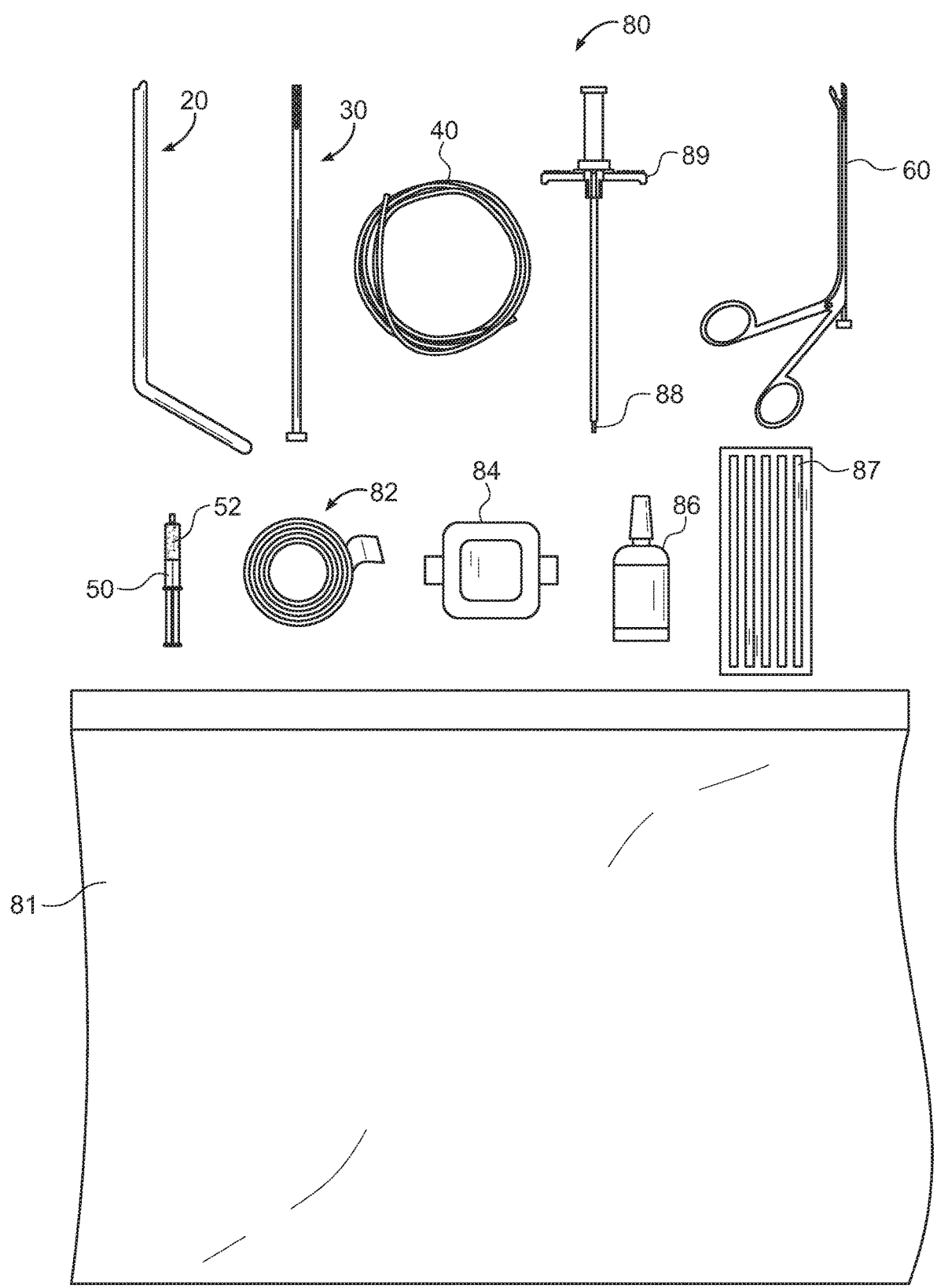
FIG. 23 is a view of a kit containing the components of an introducer system in accordance with an example embodiment.

As shown in FIG. 23, all the components needed for performing the methods and procedures described herein may conveniently be provided in a kit 80 containing an introducer of any embodiment disclosed herein (e.g., a cannula 20 and trocar 30, or alternatively, a grasper 60), along with any instruments or elements needed to perform intraoperative adductor canal blocks by a surgeon through the surgical incision under direct vision or under arthroscopic guidance.

For example, single and/or split catheters (such as a 7FR catheter) can be included in the kit 80, with single and multi-lumens to allow for placement of a catheter 40 in both the adductor canal and along the posterior capsule of the knee, thus blocking multiple nerves transmitting pain sensation around the knee. These catheters can allow for continuous delivery of medication to block sensory nerve conduction (neurotmesis) in the anterior and the posterior medial and lateral compartments of the knee.

The kit 80 may be provided in a single peel pack 81 sterile kit, or other suitable kit form. Further, in addition to the cannula, trocar, or grasper, the kit 80 may include the syringe 50, such as a 10 cc syringe, and the syringe can be filled with a nerve blocking agent 52, such as 0.5% ropivacaine. In some cases, the kit further contains gauze 82, such as 2×2 gauze, and it may also include Tegaderm 84, such as 3×3 inch Tegaderm. In some cases, the kit further contains surgical glue 86. The kit may also include Steri-Strips 87 and an introducer needle 88 and a T-Peel sheath 89, which is a proprietary device.

F. Operation.

Surgeries around the knee can be very painful, and traditionally require parental and oral opioid analgesics to provide post-operative pain relief. Significant improvements have been made in pain management over the past decades, most significantly with the use of regional block anesthesia. Traditionally, these regional nerve blocks are placed by anesthesia services using a nerve stimulator or under ultrasonic guidance. However, these anesthesia services are not always available and when available may require a significant learning curve for the anesthesiologist to provide reproducible, efficient and efficacious nerve blocks. Efficacy of these blocks is dependent on patients' body habitus and anesthesia services willingness to perform these blocks, as well as the provider's experience, training and capabilities. Placement of nerve blocks by the surgeon under direct visualization is safer, more reliable and more efficacious.

Surgeon-placed nerve blocks can also provide superior results as they can include more nerves, providing a broader scope of relief. As with any block technique standardized, equipment is needed to provide for a safe and reproducible procedure. Variability of current instruments produces risks of improper placement of the block and catheter which can lead to poorer efficacy, and possible injury to surrounding neurovascular structures. Because of variability of current instruments surgeons may dangerously place the catheter into the posterior space. Entering this space posterior to the adductor tendon can lead to potential damage to vital nerves and vascular structures. The adductor canal block introducer is specifically designed to provide catheter placements in a safe, reproducible and reliable fashion.

Surgical Approach:

The catheter can be inserted during a surgical approach to the knee. The medial parapatellar procedure is performed by incising the VMO beginning medially just above the patella and extending down to the tibial tubercle, leaving a cuff of capsular tissue on the patella for repair at closure. For the mid-vastus approach, the VMO is split in-line with the muscle fibers at the superior pole of the patella and then incised distally to the tibial tubercle. The subvastus approach to TKA begins with an incision below the VMO muscle and extends to the tibial tubercle.

1. Exposure

The surgeon will identify adductor tubercle of the epicondyle of the femur, and elevate the VMO with blunt retractors 90 (Army/Navy) to expose its deep surface and the anterior surface of the medial intermuscular septum. The medial intermuscular septum serves as the floor for catheter placement. The adductor magnus tendon can be palpated beneath the medial intermuscular septum just cephalad to the adductor tubercle. The VMO and adductor magnus muscles form the borders of the adductor canal.

2. Catheter Placement

Placement of the catheter for a continuous block is performed by inserting an introducer needle 88 and T-Peel sheath 89 from the superior lateral aspect of the knee, just above the joint at the superior pole of the patella. The introducer needle and T-Peel sheath are passed under the rectus femoris tendon and into the surgical opening. The introducer needle 88 is then removed leaving the T-Peel sheath 89 in place. The catheter 40 is then passed through the T-Peel sheath and retrieved into this potential space. The T-Peel sheath 89 is peeled away and discarded. The catheter entry point is a "potential space" that is opened with blunt dissection, during VMO retraction.

3. Advancement of the Catheter

After establishing the potential space with gentle digital dissection, the distal end of the catheter is grasped by the grasper or placed into the slotted cannula (see FIGS. 9 and 24) and advanced cephalad by blunt dissection along the anterior surface of the medial intermuscular septum and deep to the VMO. The end of the catheter is placed approximately 9-10 inches cephalad to the superior patella and is located in the space created by the muscles that make up the borders of the adductor canal. This system 10 can also be used for placement in other parts of the body. Once the catheter is placed, the retractors 90 are removed, the wound is irrigated and closed in the standard fashion of choice.

The introducer system 10 is used to insert a catheter 40 during a standard medial parapatellar, subvastus, or midvastus approach to TKA (see FIGS. 9-16 and 24-30). After the implant components have all been installed, the vastus medialis oblique (VMO) muscle is retracted at the level of the patella to expose the medial intermuscular septum (layers of deep fascia) that is anterior and intimate to the adductor tendon. After identifying the adductor tubercle of the epicondyle of the femur, the surgeon retracts the VMO with blunt retractors 90 (Army/Navy) to expose the anterior surface of the medial intermuscular septum. The medial intermuscular septum which serves as the floor for catheter placement is readily visible and lies just anterior to the adductor tendon. The adductor longus tendon can be palpated beneath the medial intermuscular septum as it inserts onto the adductor tubercle. The VMO and adductor muscles form the muscular borders of the adductor canal.

Figure 9:
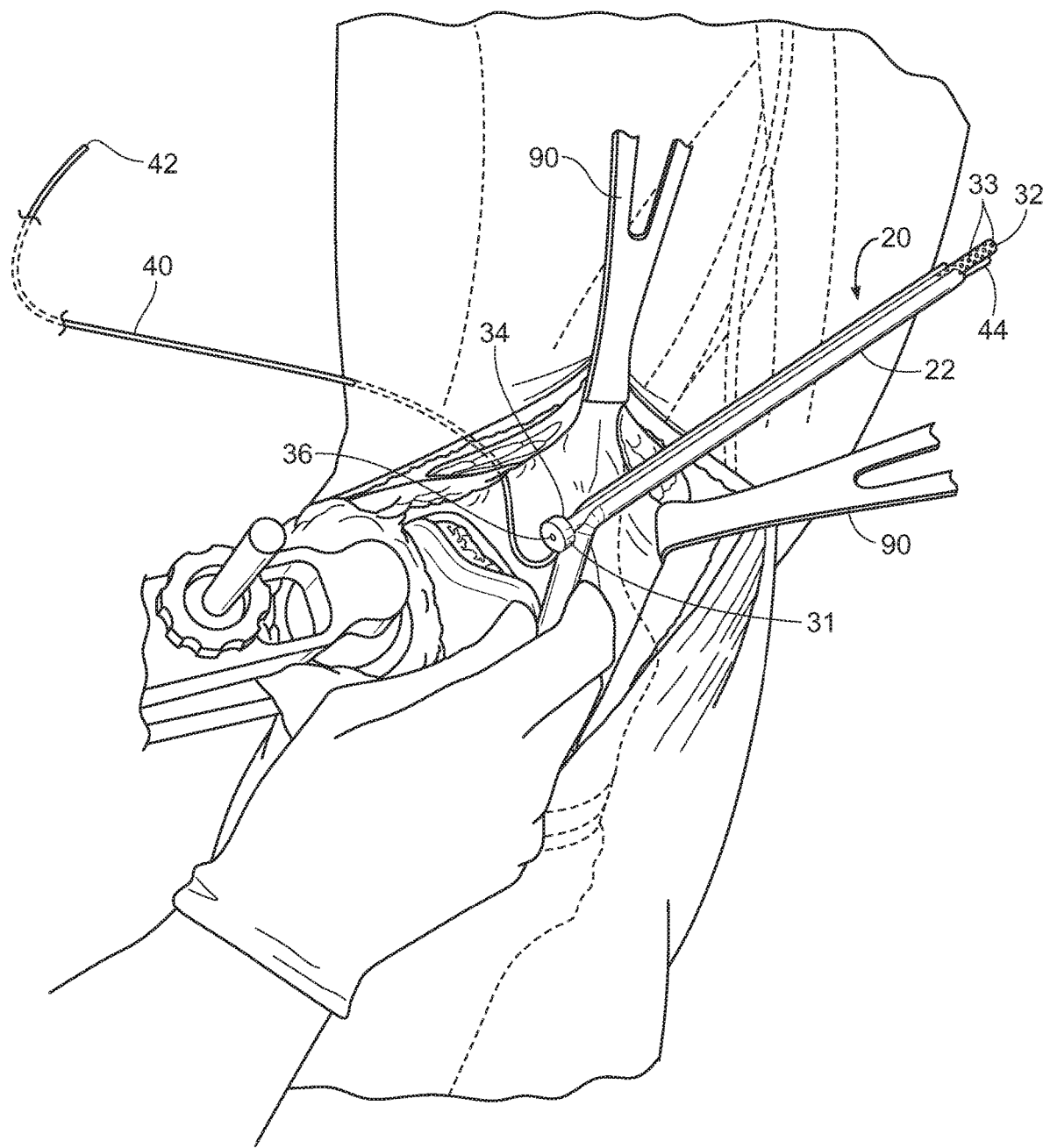
FIG. 9 is a perspective view of an introducer system in use in accordance with an example embodiment.

To use the system, opening the Introducer kit 80 (if used), the surgeon lifts out the introducer needle 88 and catheter 40. After blunt digital dissection and placement of retractors 90 under the VMO, exposing the potential space that is created by the retracted muscles that make up the borders of the adductor canal, the introducer needle 88 is inserted through the skin at the superior lateral aspect of the knee, just proximal to the patella, and advanced medially just anterior to the distal femur to appear in this potential space. FIG. 9, for example, shows this positioning of the catheter.

The catheter 40 is retrieved from the needle sheath and then placed in the adductor canal block introducer (either the slotted cannula embodiment or the grasper embodiment) and advanced cephalad along the medial intermuscular septum, deep to the VMO, and in-line with the femoral shaft. Using the introducer, the catheter 40 is advanced cephalad until the shoulder of the introducer is stopped at, or adjacent to, the level of the superior pole of the patella. This positions the distal end 44 of catheter 40 approximately 9-10 inches cephalad to the superior patella and within the space created by the muscles that make up the borders of the adductor canal. Cadaveric Studies have demonstrated this position to be ideal for maximum blocking of nerve conduction.

The final, precise placement of the catheter 40 guided by the introducer (cannula 20 or grasper 60) positions the catheter within the medial intermuscular septum of the thigh, separating the vastus medialis oblique (VMO) and adductor muscles that form the muscular borders of the adductor canal. When performing a cemented implant, the catheter can be placed while the cement is curing without adding additional time to the operative procedure.

4. Using the Slotted Cannula

Figure 10:
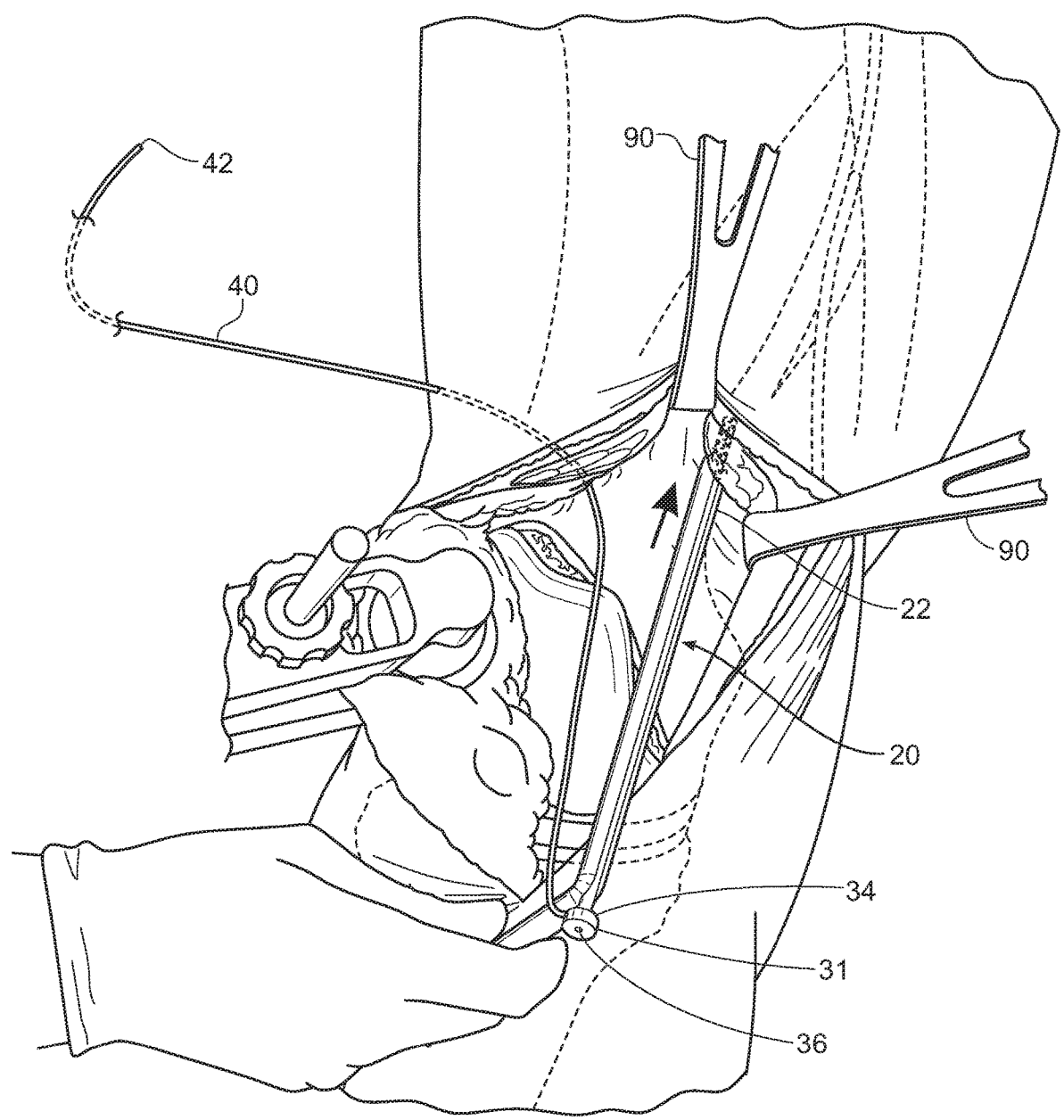
FIG. 10 is another perspective view of an introducer system in use in accordance with an example embodiment.
Figure 11:
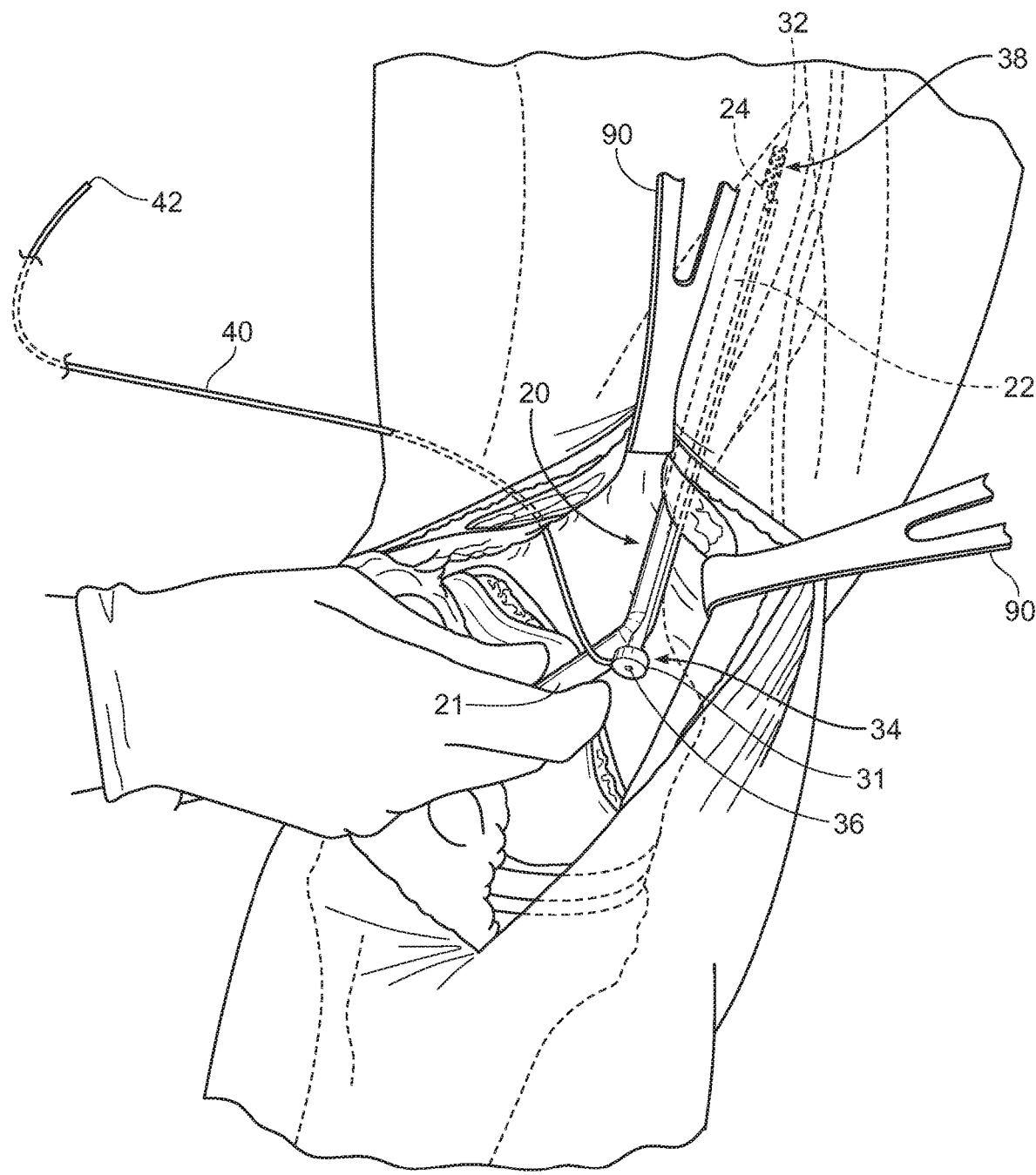
FIG. 11 is another perspective view of an introducer system in use in accordance with an example embodiment.
Figure 15:
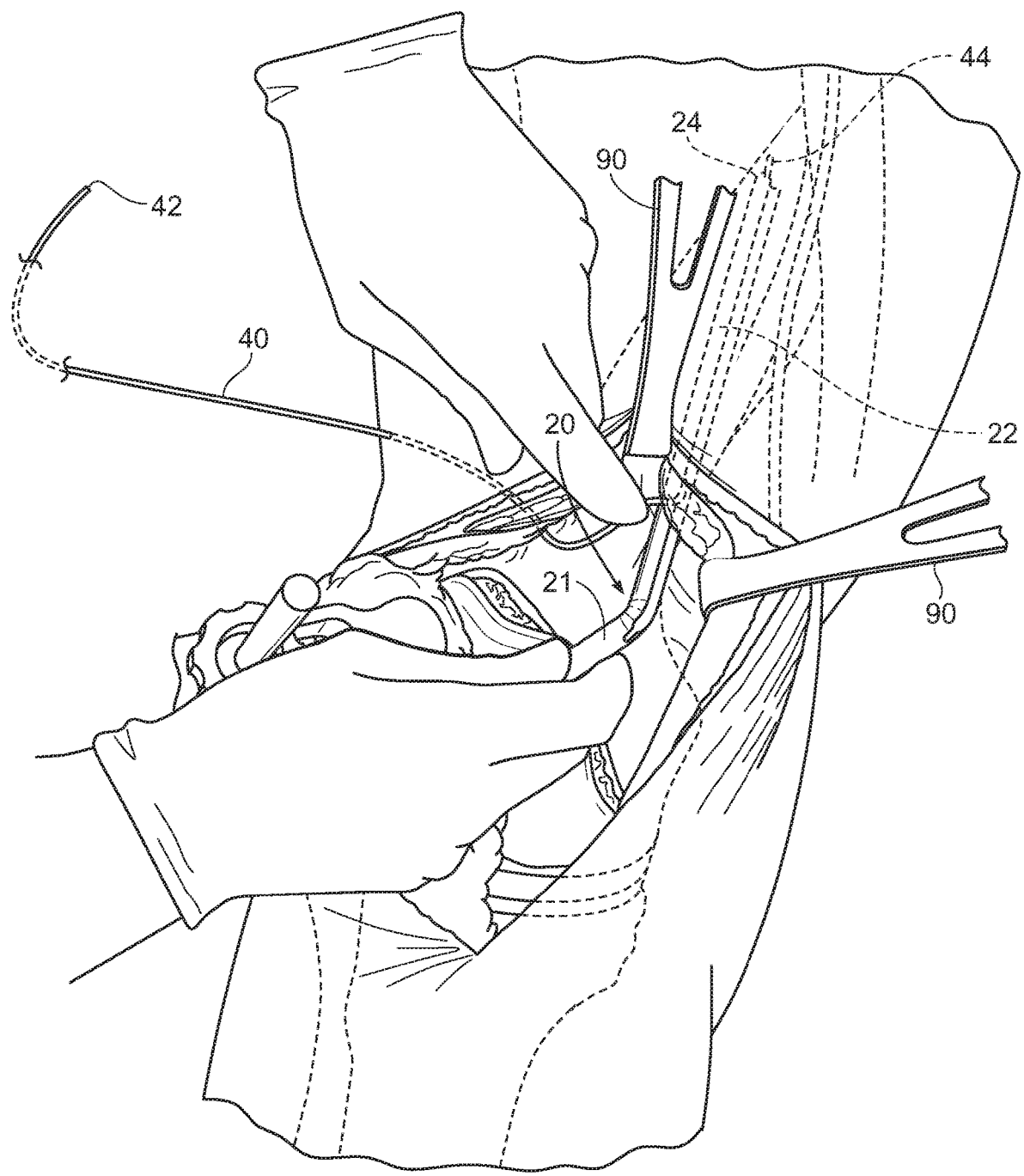
FIG. 15 is another perspective view of an introducer system in use in accordance with an example embodiment.
Figure 16:
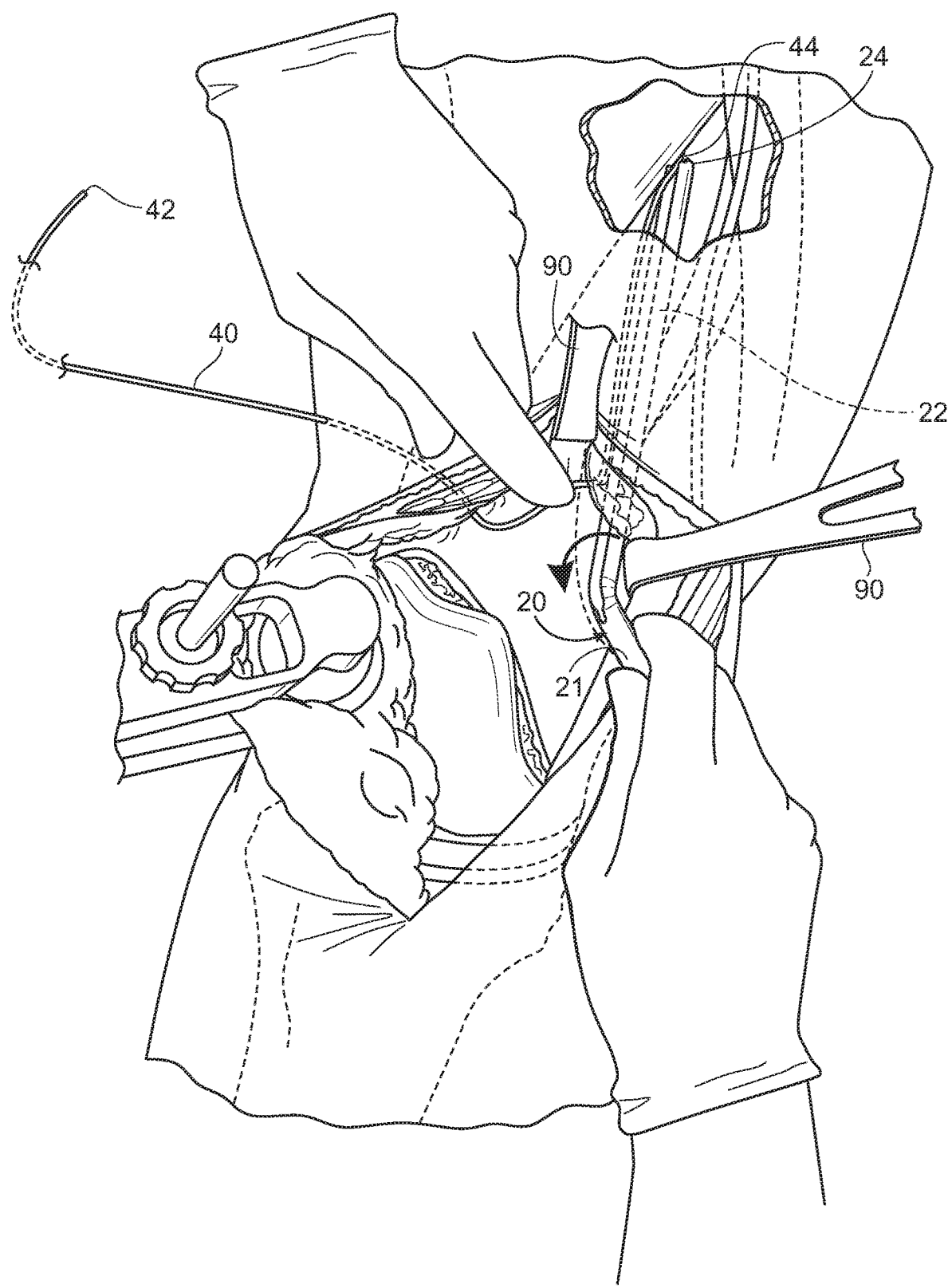
FIG. 16 is another perspective view of an introducer system in use accordance with an example embodiment.
Figure 17:
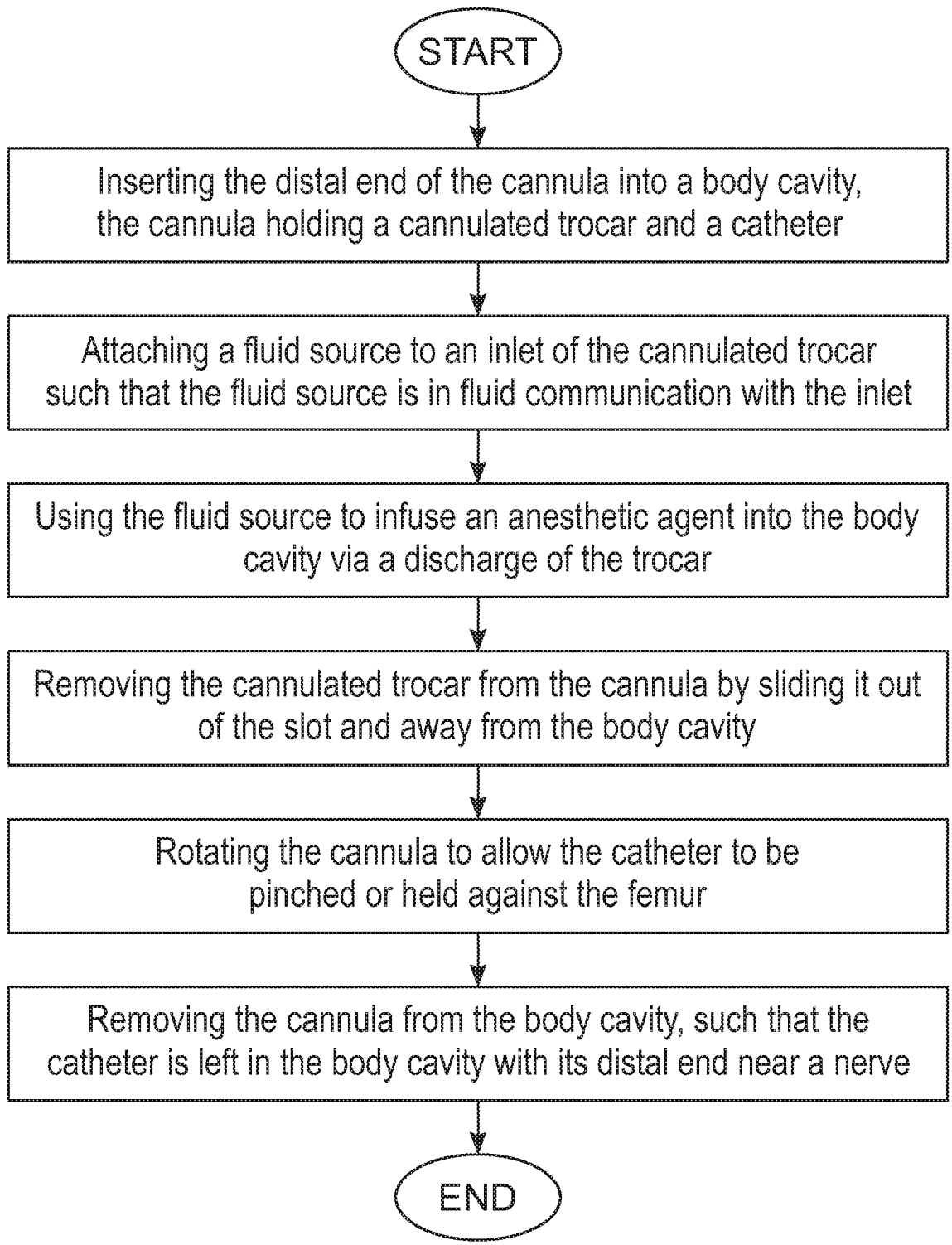
FIG. 17 is a flow chart of steps usable with an introducer system in accordance with an example embodiment.

FIGS. 9-16 illustrate the use of the introducer system with a slotted cannula, and the steps for use are broadly outlined in FIG. 17. When using the slotted cannula 20, a catheter 40 may be first be inserted in a desired position in the lower portion of slot 27, and may have its distal end 44 extending slightly beyond the distal end 24 of the cannula 20. To hold the catheter 40 in place in the lower portion of the slot, slot 27b, the trocar 30 is then slid into place in the upper portion of slot 27. As shown in FIGS. 10-11, the distal end 24 of the cannula 20 is then inserted into a body cavity, such as an adductor canal, such that the distal end 44 of catheter 40 is in a desired location for later infusion of anesthetic.

Figure 12:
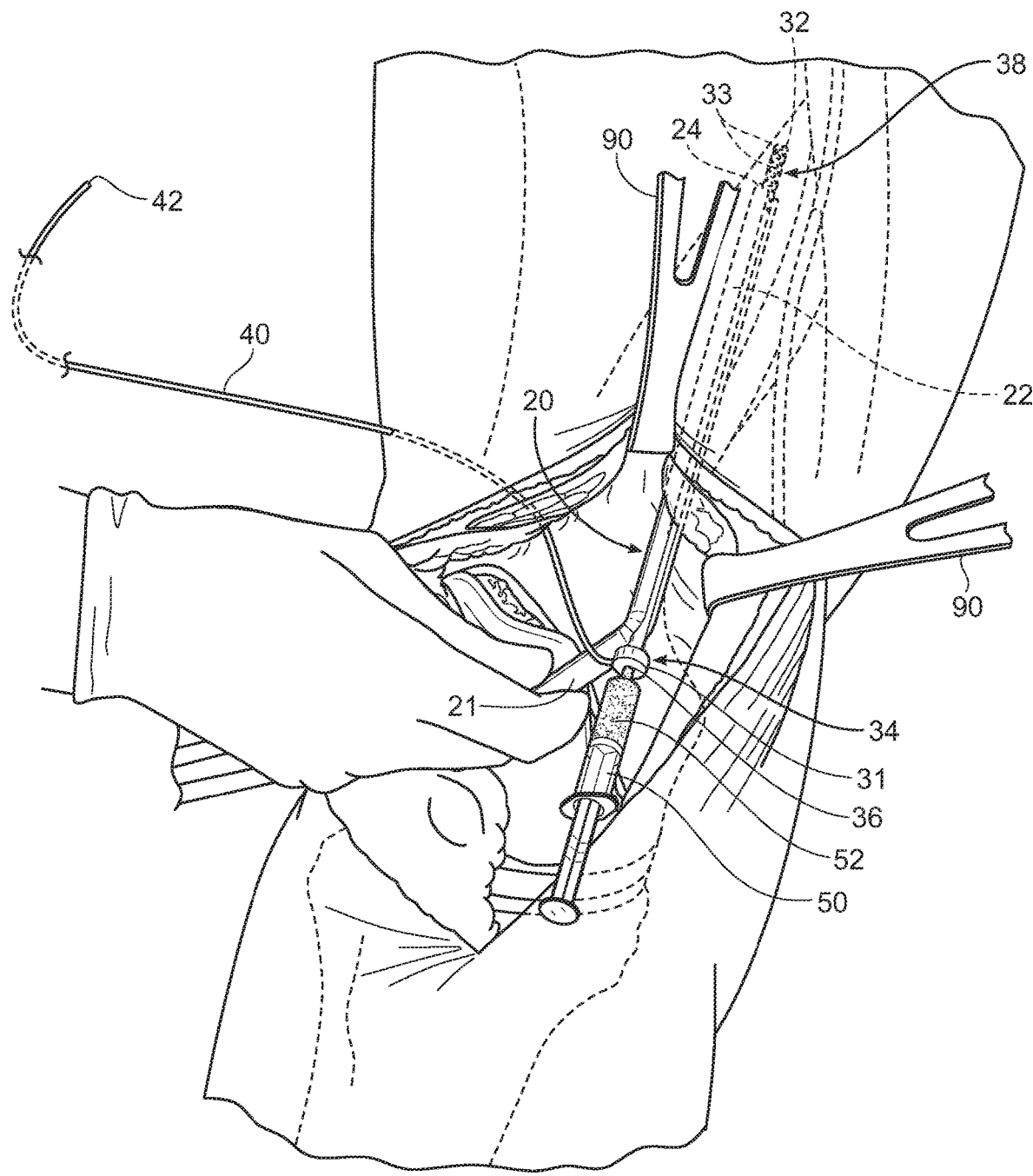
FIG. 12 is another perspective view of an introducer system in use in accordance with an example embodiment.
Figure 13:
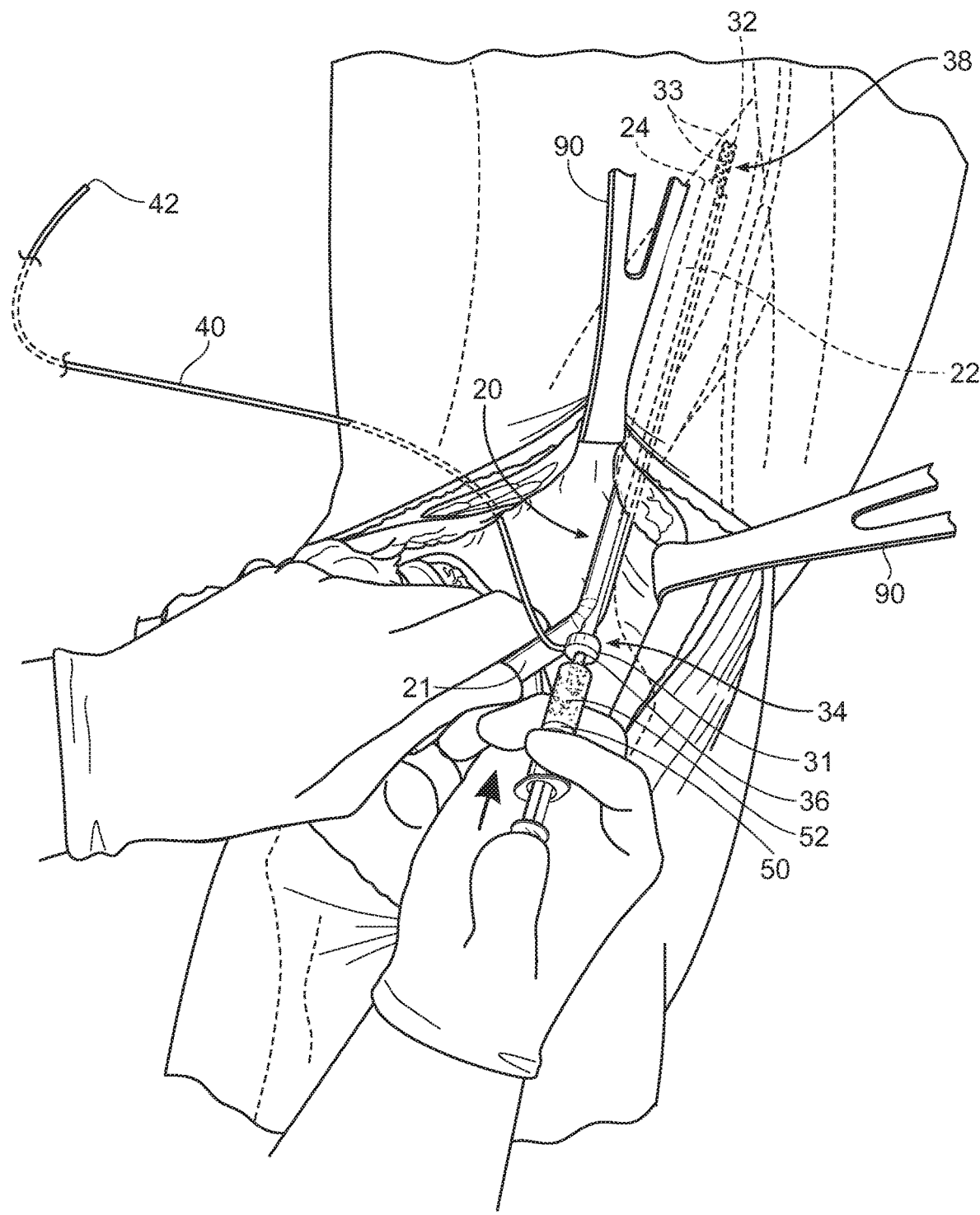
FIG. 13 is another perspective view of an introducer system in use in accordance with an example embodiment.
Figure 14:
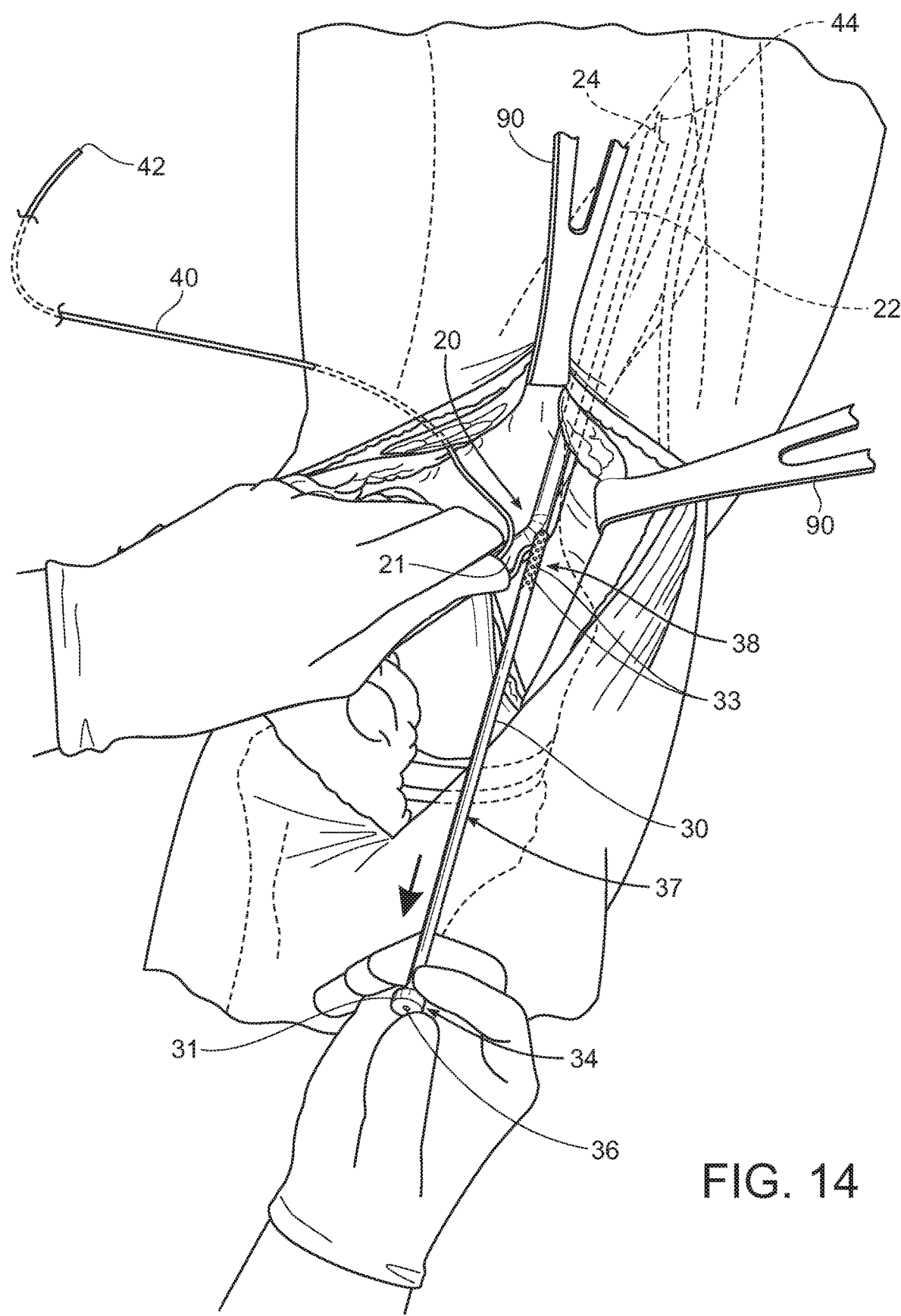
FIG. 14 is another perspective view of an introducer system in use in accordance with an example embodiment.

Next, a syringe 50 or other fluid source may be attached or locked to inlet 36 of the cannulated trocar 30, as shown in FIG. 12, and as stated, the syringe 50 or fluid source may contain a local anesthetic 52 of the physician's choice. The syringe 50 may be used to administer a bolus dose of local anesthetic (FIG. 13) through the cannulated trocar 30, and specifically, out of the discharge 38, which may comprise multiple openings 33. Once the bolus dose is administered, the trocar 30 may be removed by sliding it rearward out of the cannula 20, as shown in FIG. 14. This allows the catheter 40 to be removed from the cannula 20 as well, which may be accomplished by holding the catheter against the femur with a finger, as shown in FIGS. 15-16, and rotating the cannula so that the catheter can be held in place against the femur when the cannula is removed. With the catheter thus in its desired position, the cannula 20 may be withdrawn from the surgical opening.

5. Using the Grasper

Figure 21:
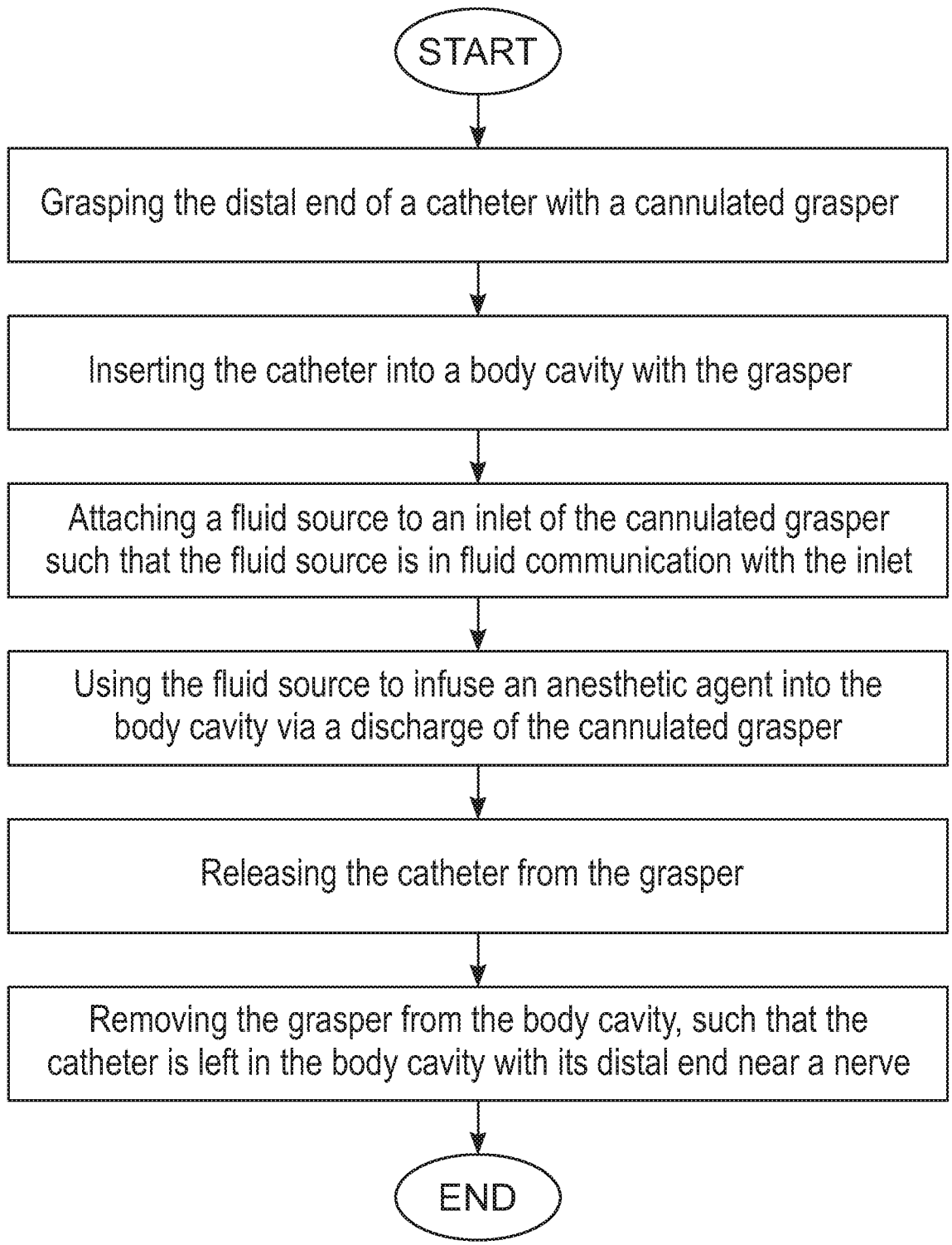
FIG. 21 is a flow chart of steps usable with an introducer system in accordance with another example embodiment.
Figure 24:
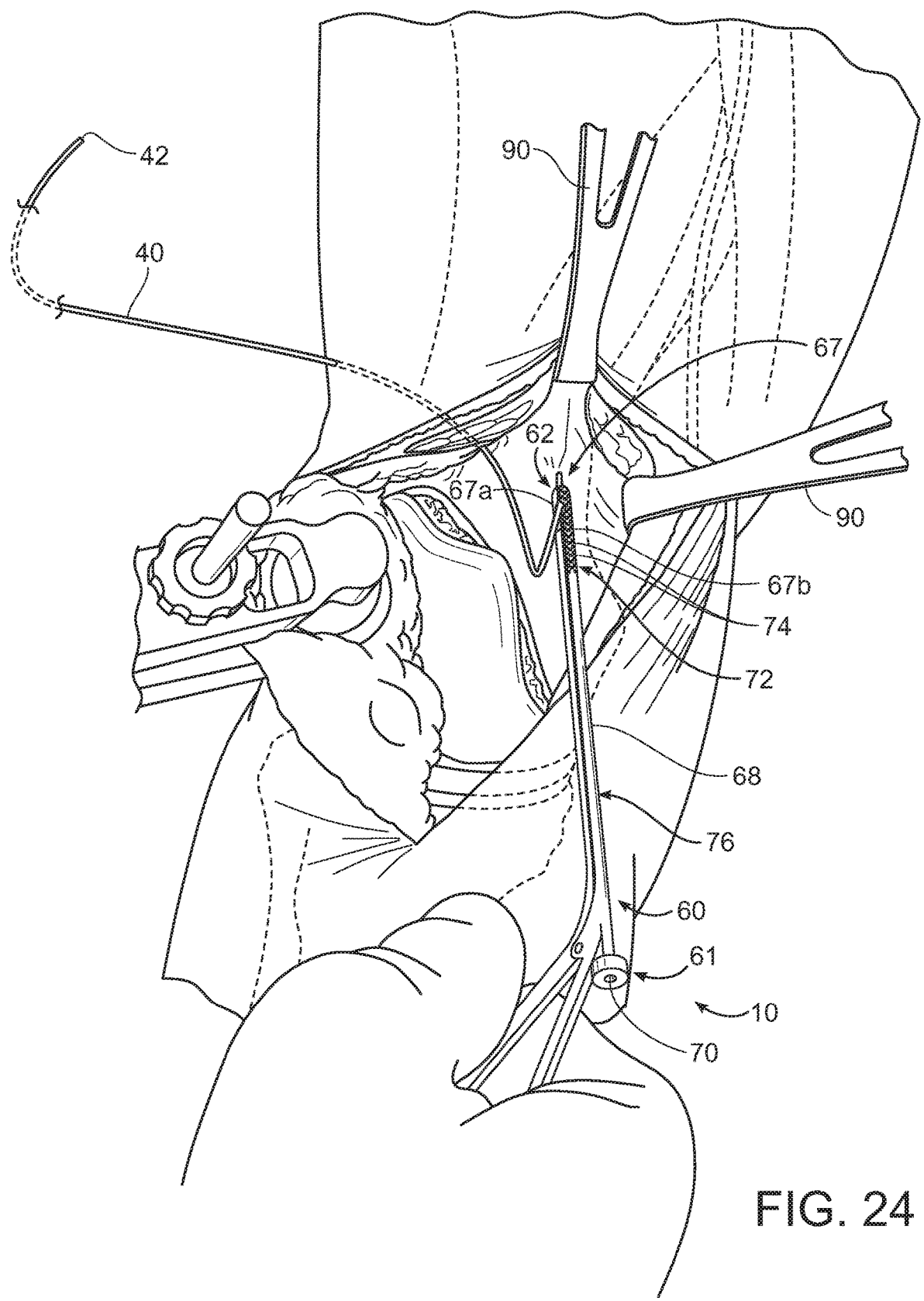
FIG. 24 is a perspective view of an introducer system in use in accordance with another example embodiment.
Figure 25:
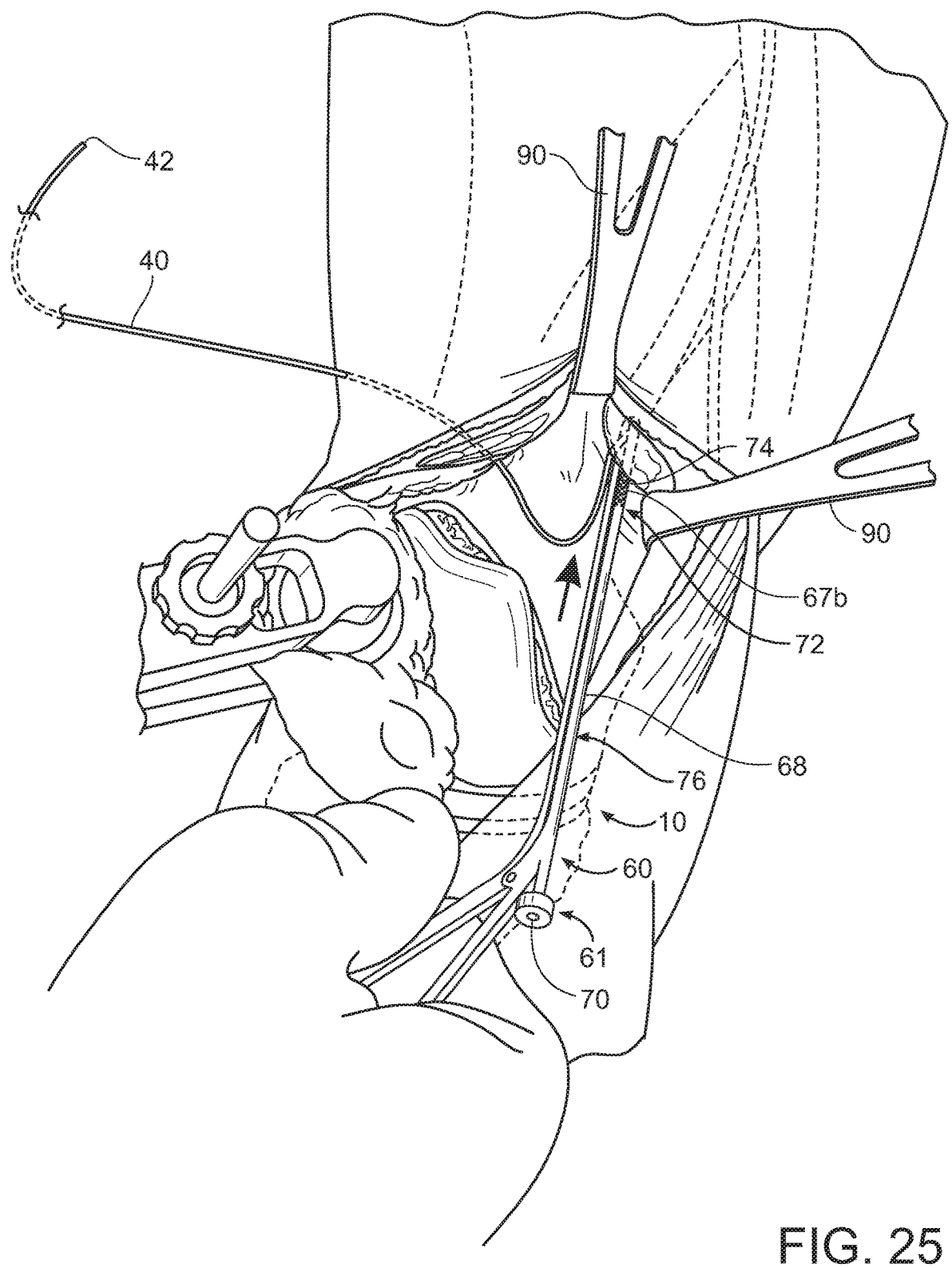
FIG. 25 is another perspective view of an introducer system in use in accordance with another example embodiment.
Figure 26:
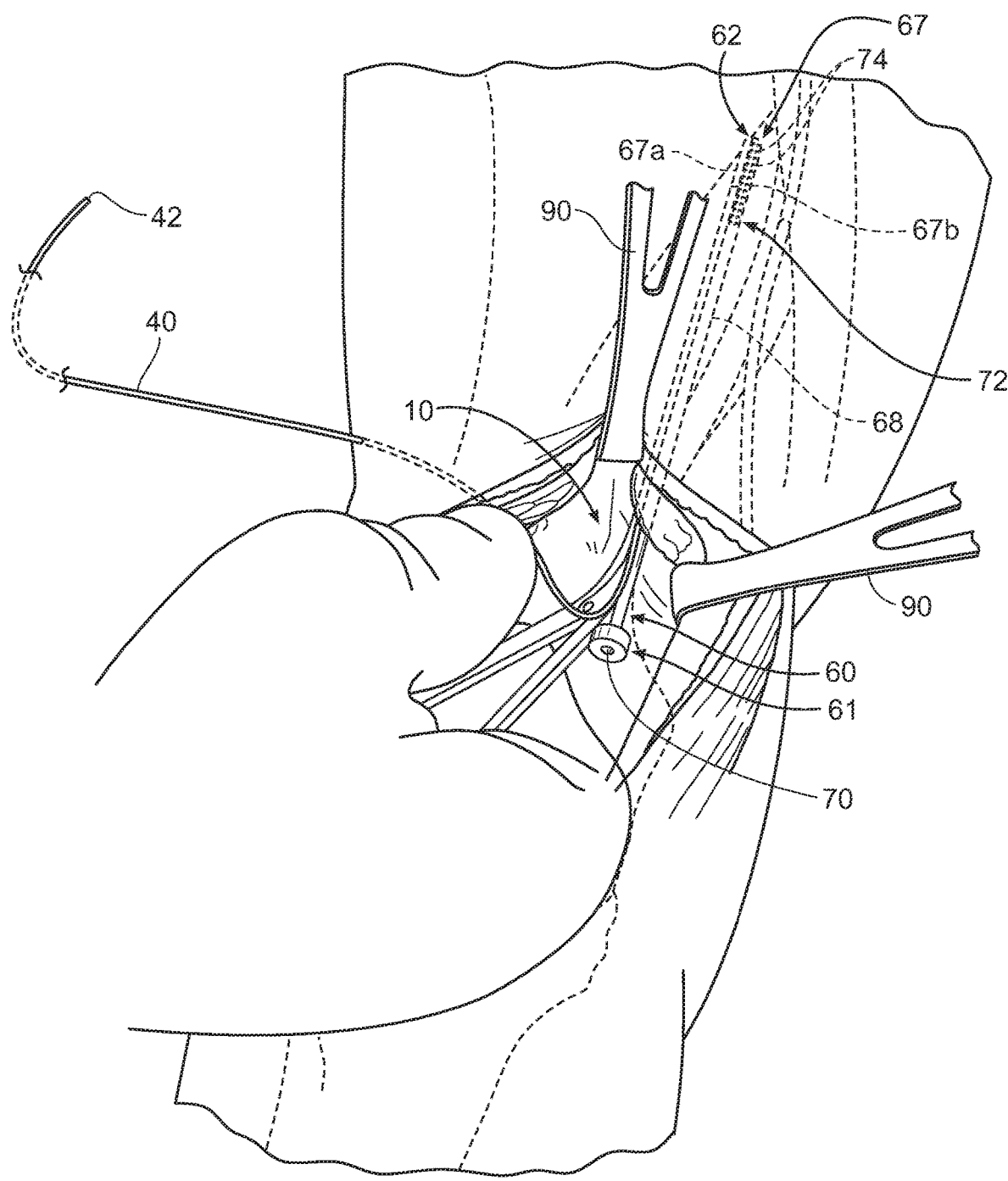
FIG. 26 is another perspective view of an introducer system in use in accordance with another example embodiment.

FIGS. 24-30 illustrate the use of the introducer system with a grasper 60, rather than a slotted cannula, and the steps for this use are broadly outlined in FIG. 21. The method is similar, except that the grasper 60 does not have a removable trocar, and instead includes a hollow elongated portion 68 with a channel 69 for carrying a local anesthetic for the bolus dose to the discharge 72, which may comprise multiple openings 74 near the distal end 62 of the grasper 60. It also uses a grasping mechanism 67 to hold the distal end 44 of the catheter 40, rather than a slot, and the mechanism is operated by handles 64 with finger loops 66. When using the grasper 60, the distal end 44 of a catheter 40 may be grasped in the grasping mechanism, between grasping members 67a and 67b, as best shown in FIGS. 18-20 and 24. As shown in FIGS. 24-25, the distal end 62 of the grasper 60 is then inserted into a body cavity, such as an adductor canal, such that the distal end 44 of catheter 40 is positioned in a desired location for later infusion of anesthetic.

Figure 27:
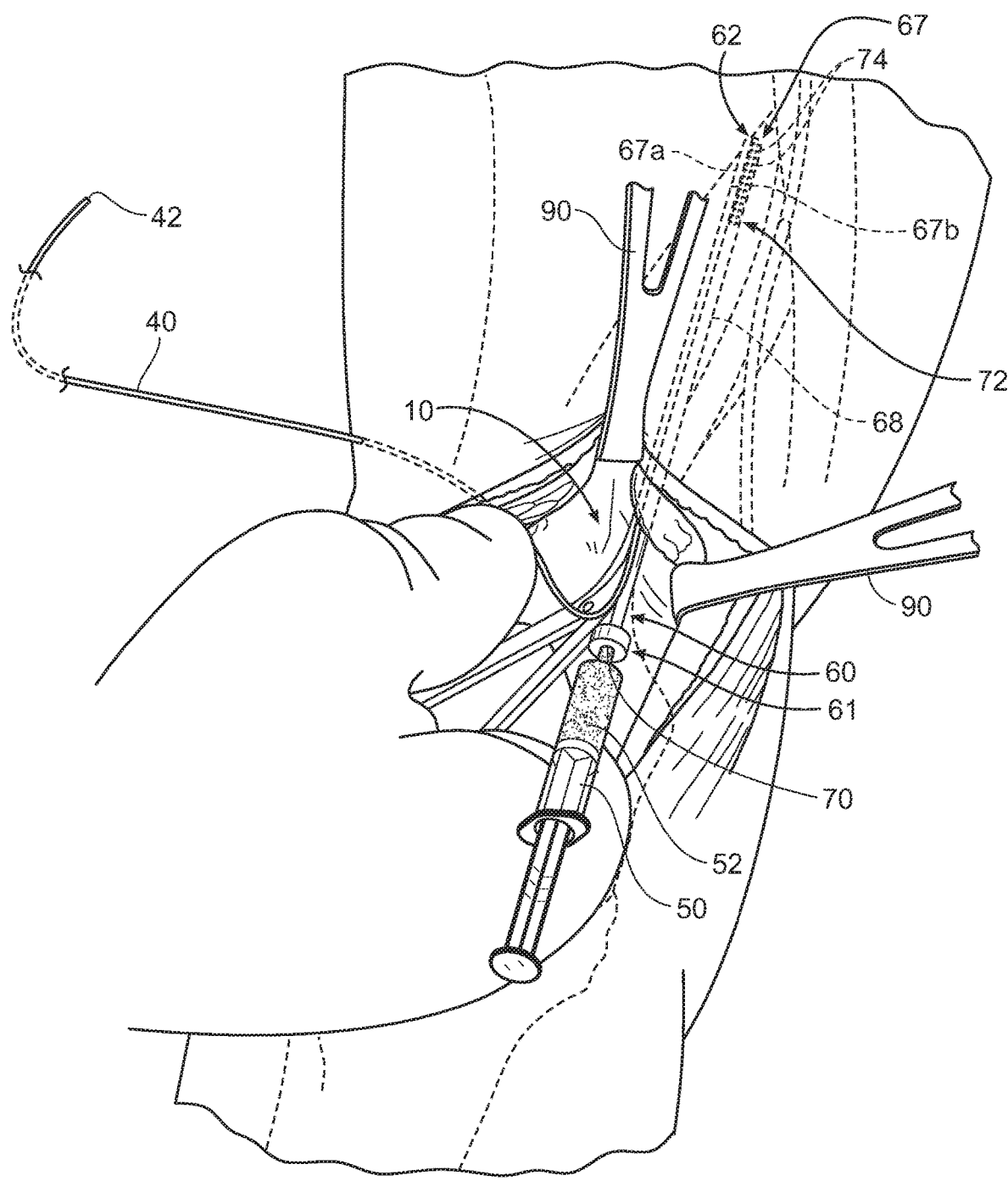
FIG. 27 is another perspective view of an introducer system in use in accordance with another example embodiment.
Figure 28:
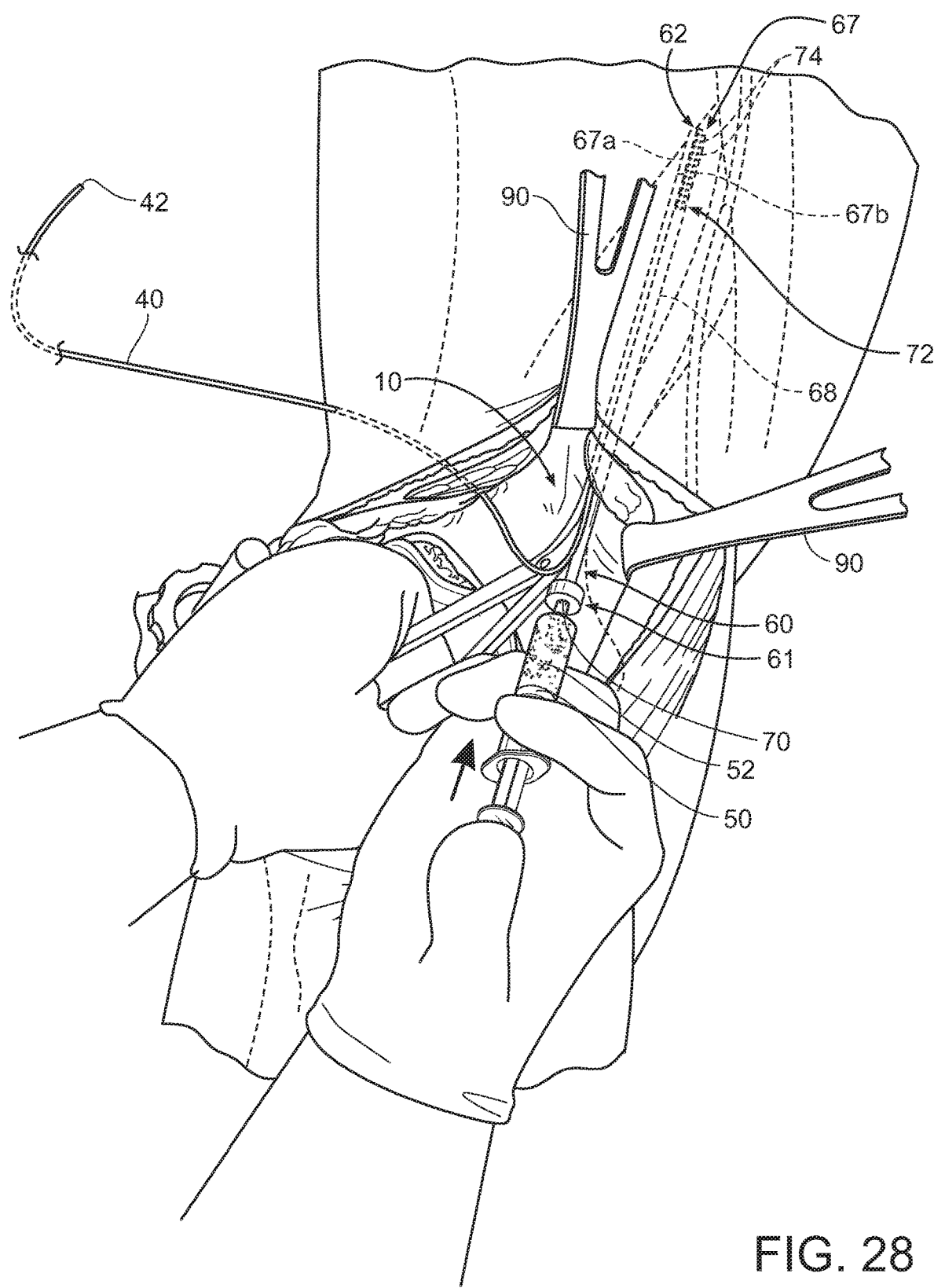
FIG. 28 is another perspective view of an introducer system in use in accordance with another example embodiment.
Figure 29:
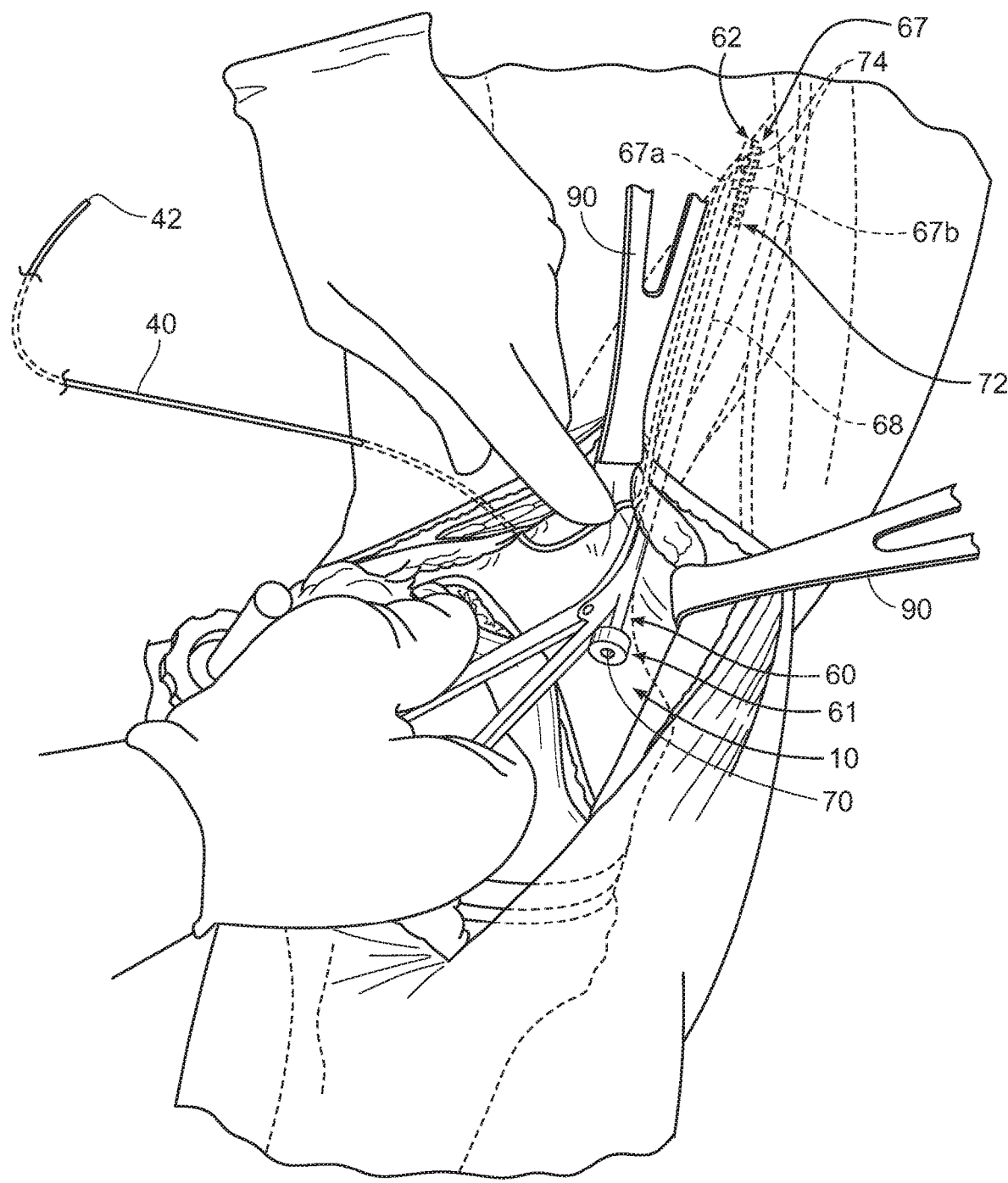
FIG. 29 is another perspective view of an introducer system in use in accordance with another example embodiment.
Figure 30:
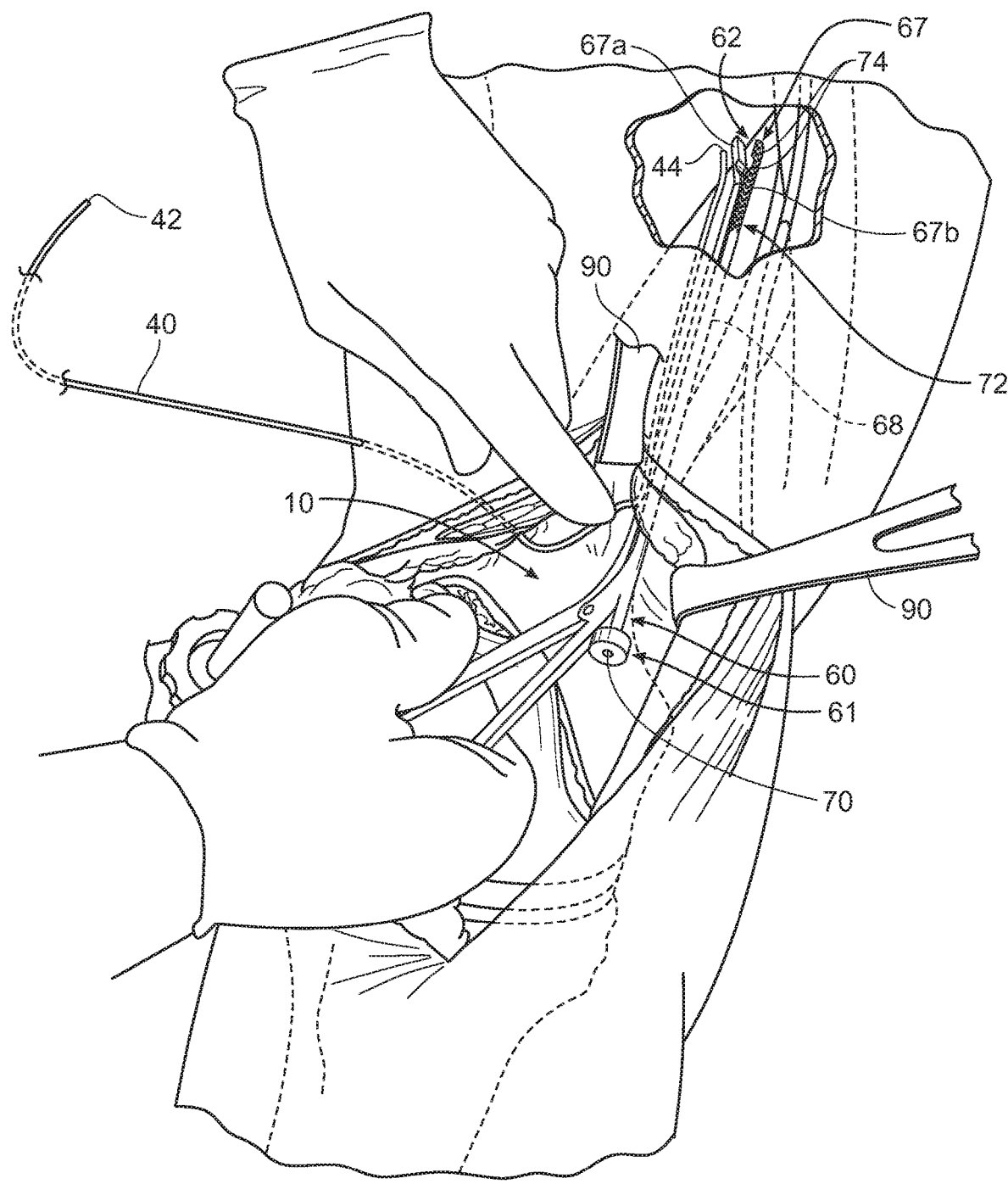
FIG. 30 is another perspective view of an introducer system in use in accordance with another example embodiment.

Next, a syringe 50 or other fluid source may be attached or locked to inlet 70, as shown in FIG. 27, and the syringe 50 or fluid source may contain a local anesthetic 52 of the physician's choice. The syringe 50 may be used to administer a bolus dose of local anesthetic (FIG. 28) through the elongated member 69, and specifically, out of the discharge 72, which may comprise multiple openings 74. Once the bolus dose is administered, the surgeon may open the grasping mechanism 67 using finger loops 66 to release the catheter 40, as shown in FIG. 30, leaving it in the desired location for administering further local anesthetic. The surgeon may also hold the catheter against the femur to ensure it stays in the desired position when the grasper 60 is withdrawn, as shown in FIGS. 29-30. With the catheter thus in its desired position, the grasper 60 may be withdrawn from the surgical opening.

Figure 22:
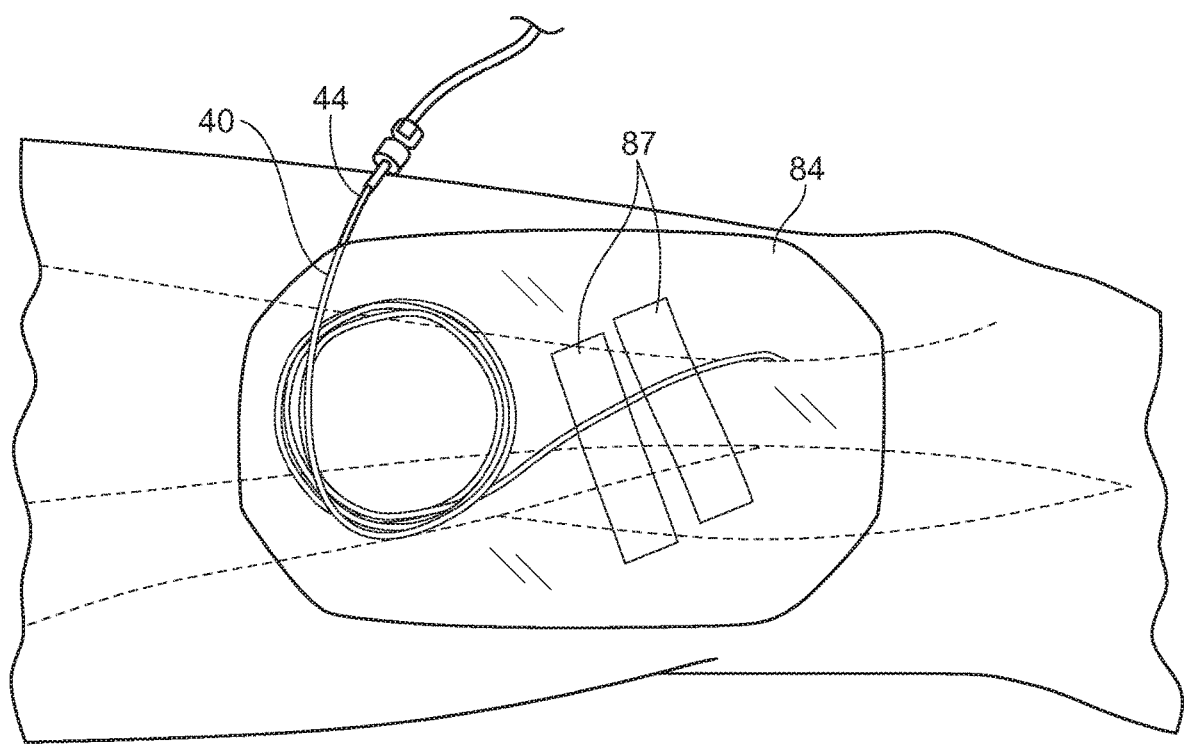
FIG. 22 is a view showing a catheter after use of an introducer system in accordance with an example embodiment.

After catheter placement with either device, once the catheter 40 is placed, the retractors 90 are removed, and the elevated muscles are allowed to return to their anatomic location. The wound is then irrigated and closed using an appropriate surgical technique. The remaining contents of the introducer kit 80 are then retrieved from the peel pack. The catheter insertion site is sealed with the surgical glue 86 and then secured with surgical strips in a "tee pee" fashion. The external portion of catheter 40 may be coiled into three 1 inch circles and held in position under the 2×2 gauze and clear adhesive, or using Steri-Strips 87 and Tegaderm 84, as shown in FIG. 22. At this point, the distal end of catheter 40 may be connected to a pump for ongoing infusion of anesthetic 52.

Unless otherwise defined, all technical and scientific terms used herein have the same meaning as commonly understood by one of ordinary skill in the art to which this invention belongs. Although methods and materials similar to or equivalent to those described herein can be used in the practice or testing of the adductor canal block introducer, suitable methods and materials are described above. All publications, patent applications, patents, and other references mentioned herein are incorporated by reference in their entirety to the extent allowed by applicable law and regulations. The adductor canal block introducer may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. A nerve block introducer system, comprising:
   a cannula having an elongated body having a distal end, a proximal end, and a slot extending along the elongated body, the slot have two sides and a lower surface;
   a cannulated trocar positioned in the slot of the cannula between the two sides, the cannulated trocar having a proximal end in fluid communication with a distal end positioned near the distal end of the cannula, wherein the proximal end of the cannulated trocar includes an inlet and the distal end of the cannulated trocar includes at least one analgesic discharge opening; and
   a catheter positioned in the slot of the cannula and held in place by the cannulated trocar, the catheter having a proximal end in fluid communication with an analgesic discharge distal end, wherein the analgesic discharge distal end is positioned near the distal end of the cannula.

2. The nerve block introducer system of claim 1, wherein the inlet is adapted for attachment of a syringe such that the syringe can be used to introduce an anesthetic agent into the inlet.

3. The nerve block introducer system of claim 1, wherein the at least one analgesic discharge opening comprises a plurality of analgesic discharge openings.

4. The nerve block introducer system of claim 3, wherein the plurality of analgesic discharge openings are located laterally on an outer surface of the cannulated trocar.

5. A method of using the system of claim 1, comprising:
   inserting the distal end of the cannula into a body cavity;
   attaching an analgesic fluid source to the inlet of the cannulated trocar such that the analgesic fluid source is in fluid communication with the inlet;
   using the analgesic fluid source to infuse an anesthetic agent into the body cavity via the at least one analgesic discharge opening;
   removing the cannulated trocar from the cannula by sliding it out of the slot and away from the body cavity; and
   removing the cannula from the body cavity, such that the catheter is left in the body cavity with the analgesic discharge distal end of the catheter near a nerve.

6. The method of claim 5, wherein the body cavity is an adductor canal and wherein the distal end of the catheter extends beyond the distal end of the cannula, the method further comprising rotating the cannula so that the catheter is held in place against the femur when the cannula is removed.

7. The method of claim 5, wherein the fluid source is a syringe.

8. The method of claim 5, wherein the at least one analgesic discharge opening comprises a plurality of analgesic discharge openings.

9. The method of claim 8, wherein the plurality of openings are located laterally on an outer surface of the cannulated trocar.

10. The nerve block introducer system of claim 1, wherein the cannulated trocar is removably positioned in the slot, such that the cannulated trocar can be removed by sliding lengthwise along the slot.

11. The nerve block introducer system of claim 1, wherein the cannulated trocar is sized and positioned such that the catheter is held in place in the slot by an interference fit.

12. The nerve block introducer system of claim 1, wherein the slot comprises a first slot portion and a second slot portion, such that the first slot portion has a larger opening between the two sides than the second slot portion, the second slot portion being positioned below the first slot portion, wherein the cannulated trocar has a larger diameter than the catheter, and wherein the cannulated trocar fits in the first slot portion and holds the catheter securely in the second slot portion.

13. The nerve block introducer system of claim 1, wherein the cannula positions the cannulated trocar and the catheter proximate a nerve of an adductor canal.

14. A kit for use in performing a nerve block procedure, the kit comprising:
   a catheter having a fluid-receiving proximal end in fluid communication with an analgesic-discharging distal end, wherein the catheter provides local anesthetic to a target nerve;
   a nerve block introducer comprising:
      a cannula having an elongated body having a distal end, a proximal end, and a slot extending along the elongated body, the slot having two sides and a lower surface;
      a cannulated trocar positioned in the slot of the cannula between the two sides, the cannulated trocar having a proximal end in fluid communication with a distal end positioned near the distal end of the cannula, wherein the proximal end of the cannulated trocar includes an inlet and the distal end of the cannulated trocar includes at least one analgesic discharge opening;
      the catheter positioned in the slot of the cannula and held in place by the cannulated trocar, and wherein the analgesic-discharging distal end is positioned near the distal end of the cannula
   an introducer needle;
   a syringe containing a nerve blocking agent, the syringe attachable to the inlet of the nerve block introducer;
   surgical glue; and
   a plurality of surgical strips.

15. The kit of claim 14, wherein the cannula of the nerve block introducer positions the cannulated trocar and the catheter proximate a nerve of an adductor canal.

16. A nerve block introducer system, comprising:
   a cannula having an elongated body having a distal end, a proximal end, and a slot extending along the elongated body, the slot having two sides and a lower surface, wherein the slot comprises a first slot portion and a second slot portion, wherein the first slot portion has a larger opening between the two sides than the second slot portion, and wherein the second slot portion is positioned below the first slot portion;
   a cannulated trocar removably positioned in the first slot portion of the cannula between the two sides such that the cannulated trocar can be removed by sliding lengthwise along the slot, the cannulated trocar having a proximal end in fluid communication with a distal end, wherein the distal end of the cannulated trocar is near the distal end of the cannula and extends beyond the distal end of the cannula, wherein the proximal end of the cannulated trocar comprises an inlet and wherein the distal end of the cannulated trocar includes a plurality of analgesic discharge openings proximate located laterally on an outer surface of the cannulated trocar beyond the distal end of the cannula, wherein the inlet of the cannulated trocar is attachable to a syringe that introduces an anesthetic agent into the inlet of the cannulated trocar with the anesthetic agent being subsequently delivered out through the plurality of analgesic discharge openings of the cannulated trocar; and a catheter positioned in the second slot portion of the cannula and held in place by an interference fit with the cannulated trocar, and by the two sides and the lower surface of the slot, the catheter comprising a proximal end in fluid communication with an analgesic discharge distal end that is positioned near the distal end of the cannula.

17. The nerve block introducer system of claim 16, wherein the cannula positions the cannulated trocar and the catheter proximate a nerve of an adductor canal.

* * * * *